US009410157B2

(12) United States Patent
Withers, III et al.

(10) Patent No.: US 9,410,157 B2
(45) Date of Patent: Aug. 9, 2016

(54) SYSTEMS AND METHODS FOR THE SECRETION OF RECOMBINANT PROTEINS IN GRAM NEGATIVE BACTERIA

(75) Inventors: Sydnor T. Withers, III, Madison, WI (US); Miguel A. Dominguez, Madison, WI (US); Matthew P. DeLisa, Ithaca, NY (US); Charles H. Haitjema, Ithaca, NY (US)

(73) Assignees: WISCONSIN ALUMNI RESEARCH FOUNDATION, Madison, WI (US); CORNELL UNIVERSITY, Ithaca, NY (US)

( * ) Notice: Subject to any disclaimer, the term of this patent is extended or adjusted under 35 U.S.C. 154(b) by 81 days.

(21) Appl. No.: 13/192,058

(22) Filed: Jul. 27, 2011

(65) Prior Publication Data

US 2012/0225453 A1 Sep. 6, 2012

Related U.S. Application Data

(60) Provisional application No. 61/369,188, filed on Jul. 30, 2010.

(51) Int. Cl.
*C12N 15/70* (2006.01)
*C12P 21/02* (2006.01)

(52) U.S. Cl.
CPC ................ *C12N 15/70* (2013.01); *C12P 21/02* (2013.01)

(58) Field of Classification Search
None
See application file for complete search history.

(56) References Cited

U.S. PATENT DOCUMENTS 7,951,361 B2 * 5/2011 Turner et al. ................ 424/93.1

OTHER PUBLICATIONS

Prehna et al., Structure 20, 1154-1166, 2012.*
Ward et al. Nature 341:544-546, 1989.*
Zhang, et al, "Extracellular accumulation of recombinant proteins fused to the carrier protein YebF in *Escherichia coli*," Nat. Biotechnol., Jan. 2006, No. 24, vol. 1, pp. 100-104.

* cited by examiner

*Primary Examiner* — Nancy T Vogel
(74) *Attorney, Agent, or Firm* — Casimir Jones S.C.

(57) ABSTRACT

Disclosed herein are systems and methods for producing recombinant proteins utilizing mutant *E. coli* strains containing expression vectors carrying nucleic acids encoding the proteins, and secretory signal sequences to direct the secretion of the proteins to the culture medium. Host cells transformed with the expression vectors are also provided.

19 Claims, 12 Drawing Sheets

FIG. 4

PLASMID MAPS

<u>pTRC99a-YebF-Cel5B (SEQ ID NO: 3)</u>

```
FEATURES             Location/Qualifiers
     source          1..6120
                     /organism="Cloning vector pTrc99A"
                     /mol_type="genomic DNA"
                     /db_xref="taxon:40992"
                     /lab_host="Escherichia coli"
                     /note="derived from pKK233-2"
     misc_feature    1..17
                     /note="derived from cloning vector pBR322"
     promoter        18..263
                     /note="trc promoter from pKK233-2"
                     /citation=[1]
     misc_feature    264..270
                     /note="NcoI/EcoRI linker"
     misc_feature    2273..2697
                     /note="5S RNA, T1, T2, rrnB"
     misc_feature    2698..4876
                     /note="derived from cloning vector pBR322"
     misc_feature    4877..4884
                     /note="BglII linker"
     misc_feature    4877..4882
                     /note="BglII linker"
     misc_feature    4883..4889
                     /note="EcoRI linker"
     misc_feature    4890..4920
                     /note="derived from plasmid RP4"
     misc_feature    4921..6107
                     /note="lacI-q region"
     misc_feature    6108..6114
                     /note="EcoRI linker"
     misc_feature    6115..6120
                     /note="BglII linker"
     misc_feature    2244..2261
                     /note="6XHis"(SEQ ID NO: 6)
     gene            291..644
                     /note="YebF"
     gene            651..2243
                     /note="Cel5B"
ORIGIN
        1 gtttgacagc ttatcatcga ctgcacggtg caccaatgct tctggcgtca ggcagccatc
       61 ggaagctgtg gtatggctgt gcaggtcgta aatcactgca taattcgtgt cgctcaaggc
      121 gcactcccgt tctggataat gttttttgcg ccgacatcat aacggttctg gcaaatattc
      181 tgaaatgagc tgttgacaat taatcatccg gctcgtataa tgtgtggaat tgtgagcgga
      241 taacaatttc acacaggaaa cagaccatgg aattcgagct cGAGAAAAAC ATGAAAAAAA
      301 GAGGGGCGTT TTTAGGGCTG TTGTTGGTTT CTGCCTGCGC ATCAGTTTTC GCTGCCAATA
      361 ATGAAACCAG CAAGTCGGTC ACTTTCCCAA AGTGTGAAGA TCTGGATGCT GCCGGAATTG
      421 CCGCGAGCGT AAAACGTGAT TATCAACAAA ATCGCGTGGC GCGTTGGGCA GATGATCAAA
      481 AAATTGTCGG TCAGGCCGAT CCCGTGGCTT GGGTCAGTTT GCAGGACATT CAGGGTAAAG
      541 ATGATAAATG GTCAGTACCG CTAACCGTGC GTGGTAAAAG TGCCGATATT CATTACCAGG
      601 TCAGCGTGGA CTGCAAAGCG GGAATGGCGG AATATCAGCG GCGTTCTAGA GATGTCGCCC
      661 CATTGAGCGT GCAAGGCAAC AAGATCCTGG CGAATGGTCA GCCGGCGAGC TTCAGCGGTA
      721 TGAGCCTGTT TTGGAGCAAT ACCGAGTGGG GTGGCGAGAA GTACTATAAC GCGCAAGTTG
      781 TTTCCTGGTT GAAATCGGAT TGGAACGCCA AGCTGGTCCG CGCAGCGATG GGTGTTGAGG
      841 ATGAAGGCGG TTACCTGACC GACCCGGCGA ATAAGGATCG CGTGACTCAA GTGGTGGACG
      901 CAGCGATCGC AAACGACATG TACGTGATCA TCGACTGGCA TAGCCATAAT GCACACCAAT
      961 ATCAGTCTCA GGCCATCGCC TTCTTTCAGG AGATGGCTCG CAAGTATGGT GCGAACAACC
```

FIG. 4, con't.

```
1021 ACGTGATCTA TGAAATCTAC AATGAGCCTT TGCAGGTGAG CTGGTCTAAC ACTATCAAAC
1081 CGTATGCCCA AGCGGTGATT GCGGCGATCC GTGCGATTGA CCCAGACAAT CTGATTATCG
1141 TGGGTACCGC GACCTGCAGC CAGGATGTCG ACGTCGCGGC GAATGACCCG ATTACGGGTT
1201 ACCAGAACAT TGCGTATACC CTGCATTTCT ATGCGGGTAC GCACGGTCAA TACCTGCGTG
1261 ATAAGGCACA GACCGCACTG AATCGTGGCA TTGCTCTGTT TGTCACCGAA TGGGGCTCGG
1321 TTAATGCCAA TGGTGATGGC GCCGTTGCTA ATAGCGAAAC CAATGCTTGG GTGAGCTTTA
1381 TGAAAACCAA TCACATCTCC AACGCGAACT GGGCACTGAA TGACAAAGTT GAGGGCGCAA
1441 GCGCATTGGT CCCGGGTGCC AGCGCAAACG GCGGCTGGGT TAACAGCCAA TTGACCGCGT
1501 CCGGCGCTCT GGCCAAAAGC ATCATCAGCG GCTGGCCGAG CTACAATACC AGCTCCAGCA
1561 GCAGCGGCGT TTCCAGCCAG ACGCAAGTCA GCAGCTCGTC CCAAGCCCCG GTCGTGTCTA
1621 GCTCTAGCAG CACGGCGTCG AGCGTGGTTA GCTCCGCTGT CAGCGGCCAA CAGTGTAACT
1681 GGTATGGTAC GTTGTATCCA CTGTGCAGCA CGACCACGAA CGGTTGGGGT TGGGAAAACA
1741 ACGCGTCGTG CATTGCGCGT GCAACGTGCA GCGGTCAGCC GGCACCGTGG GGTATCGTCG
1801 GCGGTAGCAC CAGCAGCCAA GCGTCCTCCA GCGTCCGCAG CAGCAGCAGC TCTCTGGTCA
1861 GCTCCAGCCG TAGCAGCAGC AGCAGCTCTG TTCAGTCTAG CAGCGGGCCT TCGTCGGTGG
1921 CGAGCAGCAG CGGCAGCAGC AGCGGCCAGT GCAGCTACAC CGTTACCAAT CAGTGGAGCA
1981 ACGGTTTTAC CGCATCCATC CGTATTGCGA ACAATGGCAC CAGCCCGATC AACGGTTGGA
2041 ATCTGAGCTG GACCTACTCT GACGGTAGCC GTGTTACCAA TTCTTGGAAC GCGAATGTGT
2101 CTGGCAATAA CCCATACACC GCATCTAACC TGGGTTGGAA TGGCAGCATT CAACCGGGTC
2161 AAGCTGTGGA GTTTGGCTTT CAGGGCACCA AGAATAACAG CGCTGCGGCT ATCCCGACCC
2221 TGAGCGGCAA CGTGTGCAAC AACCATCATC ACCATCACCA CTAAaagctt ggctgttttg
2281 gcggatgaga gaagattttc agcctgatac agattaaatc agaacgcaga agcggtctga
2341 taaaacagaa tttgcctggc ggcagtagcg cggtggtccc acctgacccc atgccgaact
2401 cagaagtgaa acgccgtagc gccgatggta gtgtggggtc tccccatgcg agagtaggga
2461 actgccaggc atcaaataaa acgaaaggct cagtcgaaag actgggcctt tcgttttatc
2521 tgttgtttgt cggtgaacgc tctcctgagt aggacaaatc cgccgggagc ggatttgaac
2581 gttgcgaagc aacggcccgg agggtggcgg gcaggacgcc cgccataaac tgccaggcat
2641 caaattaagc agaaggccat cctgacggat ggcctttttg cgtttctaca aactcttttt
2701 gtttattttt ctaaatacat tcaaatatgt atccgctcat gagacaataa ccctgataaa
2761 tgcttcaata atattgaaaa aggaagagta tgagtattca acatttccgt gtcgccctta
2821 ttcccttttt tgcggcattt tgccttcctg tttttgctca cccagaaacg ctggtgaaag
2881 taaaagatgc tgaagatcag ttgggtgcac gagtgggtta catcgaactg gatctcaaca
2941 gcggtaagat ccttgagagt tttcgccccg aagaacgttt tccaatgatg agcactttta
3001 aagttctgct atgtggcgcg gtattatccc gtgttgacgc cgggcaagag caactcggtc
3061 gccgcataca ctattctcag aatgacttgg ttgagtactc accagtcaca gaaaagcatc
3121 ttacggatgg catgacagta agagaattat gcagtgctgc cataaccatg agtgataaca
3181 ctgcggccaa cttacttctg acaacgatcg gaggaccgaa ggagctaacc gcttttttgc
3241 acaacatggg ggatcatgta actcgccttg atcgttggga accggagctg aatgaagcca
3301 taccaaacga cgagcgtgac accacgatgc ctacagcaat ggcaacaacg ttgcgcaaac
3361 tattaactgg cgaactactt actctagctt cccggcaaca attaatagac tggatggagg
3421 cggataaagt tgcaggacca cttctgcgct cggcccttcc ggctggctgg tttattgctg
3481 ataaatctgg agccggtgag cgtgggtctc gcggtatcat tgcagcactg gggccagatg
3541 gtaagccctc ccgtatcgta gttatctaca cgacggggag tcaggcaact atggatgaac
3601 gaaatagaca gatcgctgag ataggtgcct cactgattaa gcattggtaa ctgtcagacc
3661 aagtttactc atatatactt tagattgatt taaaacttca tttttaattt aaaaggatct
3721 aggtgaagat cctttttgat aatctcatga ccaaaatccc ttaacgtgag ttttcgttcc
3781 actgagcgtc agaccccgta gaaaagatca aaggatcttc ttgagatcct ttttttctgc
3841 gcgtaatctg ctgcttgcaa acaaaaaaac caccgctacc agcggtggtt tgtttgccgg
3901 atcaagagct accaactctt tttccgaagg taactggctt cagcagagcg cagataccaa
3961 atactgtcct tctagtgtag ccgtagttag gccaccactt caagaactct gtagcaccgc
4021 ctacatacct cgctctgcta atcctgttac cagtggctgc tgccagtggc gataagtcgt
4081 gtcttaccgg gttggactca agacgatagt taccggataa ggcgcagcgg tcgggctgaa
4141 cggggggttc gtgcacacag cccagcttgg agcgaacgac ctacaccgaa ctgagatacc
4201 tacagcgtga gctatgagaa agcgccacgc ttcccgaagg gagaaaggcg gacaggtatc
4261 cggtaagcgg cagggtcgga acaggagagc gcacgaggga gcttccaggg ggaaacgcct
4321 ggtatcttta tagtcctgtc gggtttcgcc acctctgact tgagcgtcga tttttgtgat
4381 gctcgtcagg ggggcggagc ctatggaaaa acgccagcaa cgcggccttt ttacggttcc
4441 tggccttttg ctggcctttt gctcacatgt tctttcctgc gttatcccct gattctgtgg
4501 ataaccgtat taccgccttt gagtgagctg ataccgctcg ccgcagccga acgaccgagc
4561 gcagcgagtc agtgagcgag gaagcggaag agcgcctgat gcggtatttt ctccttacgc
4621 atctgtgcgg tatttcacac cgcatatggt gcactctcag tacaatctgc tctgatgccg
```

FIG. 4, con't.

4681 catagttaag ccagtataca ctccgctatc gctacgtgac tgggtcatgg ctgcgccccg 4741 acacccgcca acacccgctg acgcgccctg acgggcttgt ctgctcccgg catccgctta 4801 cagacaagct gtgaccgtct ccgggagctg catgtgtcag aggttttcac cgtcatcacc 4861 gaaacgcgcg aggcagcaga tcaattcgcg cgcgaaggcg aagcggcatg catttacgtt 4921 gacaccatcg aatggtgcaa aacctttcgc ggtatggcat gatagcgccc ggaagagagt 4981 caattcaggg tggtgaatgt gaaaccagta acgttatacg atgtcgcaga gtatgccggt 5041 gtctcttatc agaccgtttc ccgcgtggtg aaccaggcca gccacgtttc tgcgaaaacg 5101 cgggaaaaag tggaagcggc gatggcggag ctgaattaca ttcccaaccg cgtggcacaa 5161 caactggcgg gcaaacagtc gttgctgatt ggcgttgcca cctccagtct ggccctgcac 5221 gcgccgtcgc aaattgtcgc ggcgattaaa tctcgcgccg atcaactggg tgccagcgtg 5281 gtggtgtcga tggtagaacg aagcggcgtc gaagcctgta aagcggcggt gcacaatctt 5341 ctcgcgcaac gcgtcagtgg gctgatcatt aactatccgc tggatgacca ggatgccatt 5401 gctgtggaag ctgcctgcac taatgttccg gcgttatttc ttgatgtctc tgaccagaca 5461 cccatcaaca gtattatttt ctcccatgaa gacggtacgc gactgggcgt ggagcatctg 5521 gtcgcattgg gtcaccagca aatcgcgctg ttagcgggcc cattaagttc tgtctcggcg 5581 cgtctgcgtc tggctggctg gcataaatat ctcactcgca atcaaattca gccgatagcg 5641 gaacgggaag gcgactggag tgccatgtcc ggttttcaac aaaccatgca aatgctgaat 5701 gagggcatcg ttcccactgc gatgctggtt gccaacgatc agatggcgct gggcgcaatg 5761 cgcgccatta ccgagtccgg gctgcgcgtt ggtgcggata tctcggtagt gggatacgac 5821 gataccgaag acagctcatg ttatatcccg ccgtcaacca ccatcaaaca ggattttcgc 5881 ctgctggggc aaaccagcgt ggaccgcttg ctgcaactct ctcagggcca ggcggtgaag 5941 ggcaatcagc tgttgcccgt ctcactggtg aaaagaaaaa ccaccctggc gcccaatacg 6001 caaaccgcct ctccccgcgc gttggccgat tcattaatgc agctggcacg acaggtttcc 6061 cgactggaaa gcgggcagtg agcgcaacgc aattaatgtg agttagcgcg aattgatctg

FIG. 4, con't.

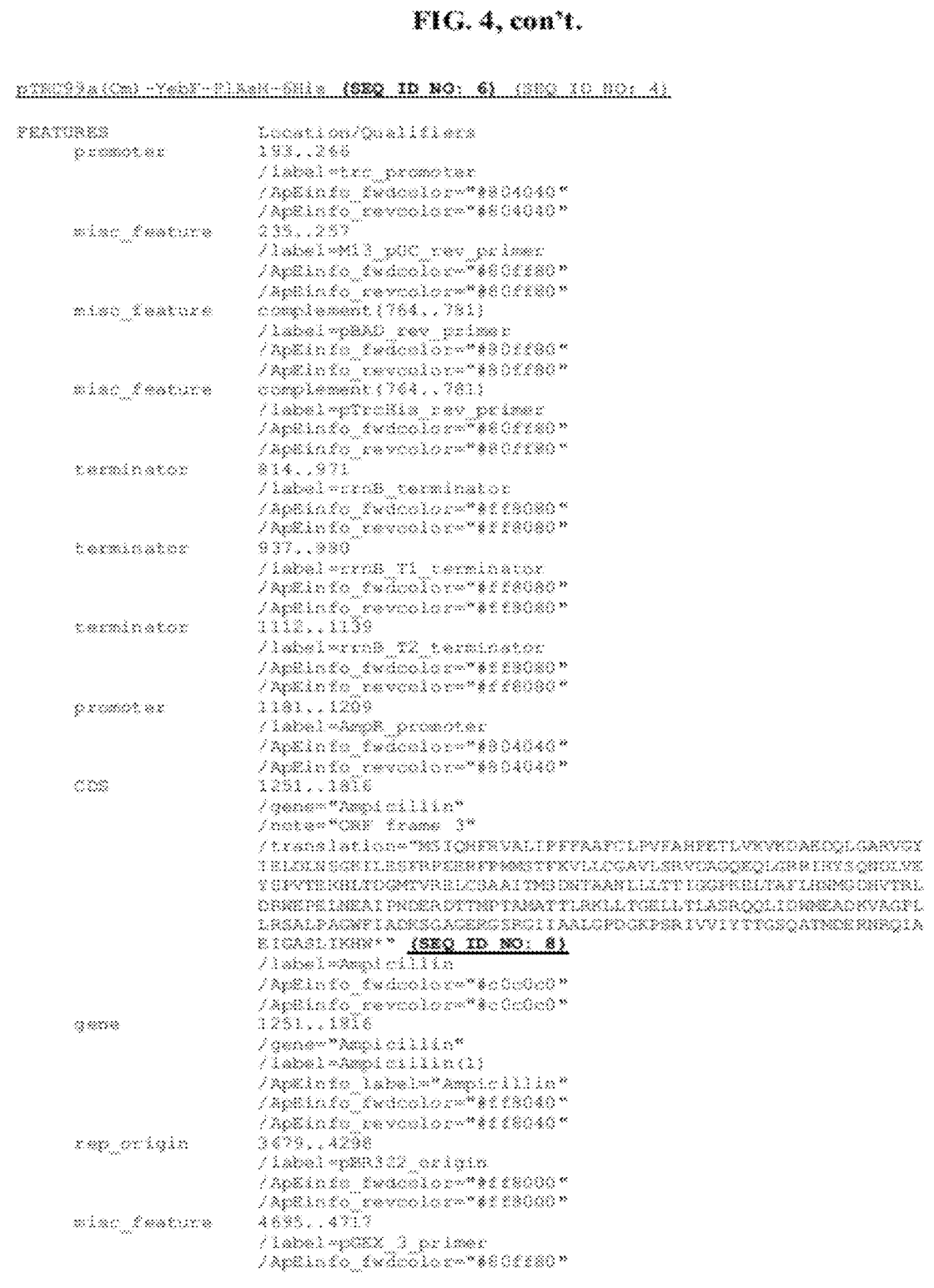

```
pTrc99a(Cm)-YebF-FlAsH-6His (SEQ ID NO: 6) (SEQ ID NO: 4)

FEATURES             Location/Qualifiers
     promoter        193..266
                     /label=trc_promoter
                     /ApEinfo_fwdcolor="#804040"
                     /ApEinfo_revcolor="#804040"
     misc_feature    235..257
                     /label=M13_pUC_rev_primer
                     /ApEinfo_fwdcolor="#80ff80"
                     /ApEinfo_revcolor="#80ff80"
     misc_feature    complement(764..781)
                     /label=pBAD_rev_primer
                     /ApEinfo_fwdcolor="#80ff80"
                     /ApEinfo_revcolor="#80ff80"
     misc_feature    complement(764..781)
                     /label=pTrcHis_rev_primer
                     /ApEinfo_fwdcolor="#80ff80"
                     /ApEinfo_revcolor="#80ff80"
     terminator      814..971
                     /label=rrnB_terminator
                     /ApEinfo_fwdcolor="#ff8080"
                     /ApEinfo_revcolor="#ff8080"
     terminator      937..980
                     /label=rrnB_T1_terminator
                     /ApEinfo_fwdcolor="#ff8080"
                     /ApEinfo_revcolor="#ff8080"
     terminator      1112..1139
                     /label=rrnB_T2_terminator
                     /ApEinfo_fwdcolor="#ff8080"
                     /ApEinfo_revcolor="#ff8080"
     promoter        1181..1209
                     /label=AmpR_promoter
                     /ApEinfo_fwdcolor="#804040"
                     /ApEinfo_revcolor="#804040"
     CDS             1251..1816
                     /gene="Ampicillin"
                     /note="ORF frame 3"
                     /translation="MSIQHFRVALIPFFAAFCLPVFAHPETLVKVKDAEDQLGARVGY
                     IELDLNSGKILESFRPEERFPMMSTFKVLLCGAVLSRVDAGQEQLGRRIHYSQNDLVE
                     YSPVTEKHLTDGMTVRELCSAAITMSDNTAANLLLTTIGGPKELTAFLHNMGDHVTRL
                     DRWEPELNEAIPNDERDTTMPTAMATTLRKLLTGELLTLASRQQLIDWMEADKVAGPL
                     LRSALPAGWFIADKSGAGERGSRGIIAALGPDGKPSRIVVIYTTGSQATMDERNRQIA
                     EIGASLIKHW*" (SEQ ID NO: 8)
                     /label=Ampicillin
                     /ApEinfo_fwdcolor="#c0c0c0"
                     /ApEinfo_revcolor="#c0c0c0"
     gene            1251..1816
                     /gene="Ampicillin"
                     /label=Ampicillin(1)
                     /ApEinfo_label="Ampicillin"
                     /ApEinfo_fwdcolor="#ff8040"
                     /ApEinfo_revcolor="#ff8040"
     rep_origin      3679..4298
                     /label=pBR322_origin
                     /ApEinfo_fwdcolor="#ff8000"
                     /ApEinfo_revcolor="#ff8000"
     misc_feature    4695..4717
                     /label=pGEX_3_primer
                     /ApEinfo_fwdcolor="#80ff80"
```

FIG. 4, con't.

```
          /ApEinfo_revcolor="#80ff80"
           misc_feature    4864..5955
                 /label=lacI
                 /ApEinfo_fwdcolor="#80ff80"
                 /ApEinfo_revcolor="#80ff80"
     CDS         4996..5955
                 /translation="MAELNYIPNRVAQQLAGKQSLLIGVATSSLALHAPSQIVAAIKS
                 RADQLGASVVVSMVERSGVEACKAAVHNLLAQRVSGLIINYPLDDQDAIAVEAACTNV
                 PALFLDVSDQTPINSIIFSHEDGTRLGVEHLVALGHQQIALLAGPLSSVSARLRLAGW
                 HKYLTRNQIQPIAEREGDWSAMSGFQQTMQMLNEGIVPTAMLVANDQMALGAMRAITE
                 SGLRVGADISVVGYDDTEDSSCYIPPSTTIKQDFRLLGQTSVDRLLQLSQGQAVKGNQ
                 LLPVSLVKRKTTLAPNTQTASPRALADSLMQLARQVSRLESGQ*" (SEQ ID NO: 9)
                 /label=ORF frame 1
                 /ApEinfo_fwdcolor="#c0c0c0"
                 /ApEinfo_revcolor="#c0c0c0"
     CDS         3231..3524
                 /gene="Ampicillin"
                 /note="ORF frame 3"
                 /translation="MSIQHFRVALIPFFAAFCLPVFAHPETLVKVKDAEDQLGARVGY
                 IELDLNSGKILESFRPEERFPMMSTFKVLLCGAVLSRVDAGQEQLGRRIHYSQNDLVE
                 YSPVTEKHLTDGMTVRELCSAAITMSDNTAANLLLTTIGGPKELTAFLHNMGDHVTRL
                 DRWEPELNEAIPNDERDTTMPTAMATTLRKLLTGELLTLASRQQLIDWMEADKVAGPL
                 LRSALPAGWFIADKSGAGERGSRGIIAALGPDGKPSRIVVIYTTGSQATMDERNRQIA
                 EIGASLIKHW*" (SEQ ID NO: 8)
                 /label=Ampicillin(2)
                 /ApEinfo_label="Ampicillin"
                 /ApEinfo_fwdcolor="#c0c0c0"
                 /ApEinfo_revcolor="#c0c0c0"
     gene        3231..3524
                 /gene="Ampicillin"
                 /label=Ampicillin(3)
                 /ApEinfo_label="Ampicillin"
                 /ApEinfo_fwdcolor="#ff8040"
                 /ApEinfo_revcolor="#ff8040"
     misc_feature 1817..3230
                 /label=CmR
                 /ApEinfo_fwdcolor="#008040"
                 /ApEinfo_revcolor="#008040"
     misc_feature 681..698
                 /note="6XHis" (SEQ ID NO: 6)
     misc_binding 645..680
                 /note="FlAsH"
     gene        291..644
                 /note="YebF"
ORIGIN
        1 gtttgacagc ttatcatcga ctgcacggtg caccaatgct tctggcgtca ggcagccatc
       61 ggaagctgtg gtatggctgt gcaggtcgta aatcactgca taattcgtgt cgctcaaggc
      121 gcactcccgt tctggataat gttttttgcg ccgacatcat aacggttctg gcaaatattc
      181 tgaaatgagc tgttgacaat taatcatccg gctcgtataa tgtgtggaat tgtgagcgga
      241 taacaatttc acacaggaaa cagaccATGG AATTCGAGCT CGAGAAAAAC ATGAAAAAAA
      301 GAGGGGCGTT TTTAGGGCTG TTGTTGGTTT CTGCCTGCGC ATCAGTTTTC GCTGCCAATA
      361 ATGAAACCAG CAAGTCGGTC ACTTTCCCAA AGTGTGAAGA TCTGGATGCT GCCGGAATTG
      421 CCGCGAGCGT AAAACGTGAT TATCAACAAA ATCGCGTGGC GCGTTGGGCA GATGATCAAA
      481 AAATTGTCGG TCAGGCCGAT CCCGTGGCTT GGGTCAGTTT GCAGGACATT CAGGGTAAAG
      541 ATGATAAATG GTCAGTACCG CTAACCGTGC GTGGTAAAAG TGCCGATATT CATTACCAGG
      601 TCAGCGTGGA CTGCAAAGCG GGAATGGCGG AATATCAGCG GCGTTTTCTG AACTGCTGCC
      661 CGGGCTGCTG CATGGAACCG CATCATCACC ATCACCACTA Atctagagtc gacctgcagg
      721 catgcaagct tggctgtttt ggcggatgag agaagatttt cagcctgata cagattaaat
      781 cagaacgcag aagcggtctg ataaaacaga atttgcctgg cggcagtagc gcggtggtcc
      841 cacctgaccc catgccgaac tcagaagtga aacgccgtag cgccgatggt agtgtggggt
```

FIG. 4, con't.

```
 901 ctccccatgc gagagtaggg aactgccagg catcaaataa aacgaaaggc tcagtcgaaa
 961 gactgggcct ttcgttttat ctgttgtttg tcggtgaacg ctctcctgag taggacaaat
1021 ccgccgggag cggatttgaa cgttgcgaag caacggcccg gagggtggcg ggcaggacgc
1081 ccgccataaa ctgccaggca tcaaattaag cagaaggcca tcctgacgga tggccttttt
1141 gcgtttctac aaactctttt tgtttatttt tctaaataca ttcaaatatg tatccgctca
1201 tgagacaata accctgataa atgcttcaat aatattgaaa aaggaagagt atgagtattc
1261 aacatttccg tgtcgccctt attccctttt ttgcggcatt ttgccttcct gtttttgctc
1321 acccagaaac gctggtgaaa gtaaaagatg ctgaagatca gttgggtgca cgagtgggtt
1381 acatcgaact ggatctcaac agcggtaaga tccttgagag ttttcgcccc gaagaacgtt
1441 ttccaatgat gagcactttt aaagttctgc tatgtggcgc ggtattatcc cgtgttgacg
1501 ccgggcaaga gcaactcggt cgccgcatac actattctca gaatgacttg gttgagtact
1561 caccagtcac agaaaagcat cttacggatg gcatgacagt aagagaatta tgcagtgctg
1621 ccataaccat gagtgataac actgcggcca acttacttct gacaacgatc ggaggaccga
1681 aggagctaac cgcttttttg cacaacatgg gggatcatgt aactcgcctt gatcgttggg
1741 aaccggagct gaatgaagcc ataccaaacg acgagcgtga caccacgatg cctacagcaa
1801 tggcaacaac gttgcgtaag aggttccaac tttcaccata atgaaataag atcactaccg
1861 ggcgtatttt ttgagttatc gagattttca ggagctaagg aagctaaaat ggagaaaaaa
1921 atcactggat ataccaccgt tgatatatcc caatggcatc gtaaagaaca ttttgaggca
1981 tttcagtcag ttgctcaatg tacctataac cagaccgttc agctggatat tacggccttt
2041 ttaaagaccg taaagaaaaa taagcacaag ttttatccgg cctttattca cattcttgcc
2101 cgcctgatga atgctcatcc ggaattccgt atggcaatga aagacggtga gctggtgata
2161 tgggatagtg ttcacccttg ttacaccgtt ttccatgagc aaactgaaac gttttcatcg
2221 ctctggagtg aataccacga cgatttccgg cagtttctac acatatattc gcaagatgtg
2281 gcgtgttacg gtgaaaacct ggcctatttc cctaaagggt ttattgagaa tatgtttttc
2341 gtctcagcca atccctgggt gagtttcacc agttttgatt taaacgtggc caatatggac
2401 aacttcttcg cccccgtttt caccatgggc aaatattata cgcaaggcga caaggtgctg
2461 atgccgctgg cgattcaggt tcatcatgcc gtctgtgatg gcttccatgt cggcagaatg
2521 cttaatgaat tacaacagta ctgcgatgag tggcagggcg gggcgtaatt tttttaaggc
2581 agttattggt gcccttaaac gcctggtgct acgcctgaat aagtgataat aagcggatga
2641 atggcagaaa ttcgaaagca aattcgaccc ggtcgtcggt tcagggcagg gtcgttaaat
2701 agccgcttat gtctattgct ggtttaccgg tttattgact accggaagca gtgtgaccgt
2761 gtgcttctca aatgcctgag gccagtttgc tcaggctctc cccgtggagg taataattga
2821 cgatatgatc atttattctg cctcccagag cctgataaaa acggttagcg cttcgttaat
2881 acagatgtag gtgttccaca gggtagccag cagcatcctg cgatgcagat ccggaacata
2941 atggtgcagg gcgcttgttt cggcgtgggt atggtggcag gccccgtggc cgggggactg
3001 ttgggcgctg ccggcacctg tcctacgagt tgcatgataa agaagacagt cataagtgcg
3061 gcgacgatag tcatgccccg cgcccaccgg aaggagctac cggacagcgg tgcggactgt
3121 tgtaactcag aataagaaat gaggccgctc atggcgttga ctctcagtca tagtatcgtg
3181 gtatcaccgg ttggttccac tctctgttgc gggcaacttc agcagcacgc aaactattaa
3241 ctggcgaact acttactcta gcttcccggc aacaattaat agactggatg gaggcggata
3301 aagttgcagg accacttctg cgctcggccc ttccggctgg ctggtttatt gctgataaat
3361 ctggagccgg tgagcgtggg tctcgcggta tcattgcagc actggggcca gatggtaagc
3421 cctcccgtat cgtagttatc tacacgacgg ggagtcaggc aactatggat gaacgaaata
3481 gacagatcgc tgagataggt gcctcactga ttaagcattg gtaactgtca gaccaagttt
3541 actcatatat actttagatt gatttaaaac ttcattttta atttaaaagg atctaggtga
3601 agatcctttt tgataatctc atgaccaaaa tcccttaacg tgagttttcg ttccactgag
3661 cgtcagaccc cgtagaaaag atcaaaggat cttcttgaga tccttttttt ctgcgcgtaa
3721 tctgctgctt gcaaacaaaa aaaccaccgc taccagcggt ggtttgtttg ccggatcaag
3781 agctaccaac tctttttccg aaggtaactg gcttcagcag agcgcagata ccaaatactg
3841 tccttctagt gtagccgtag ttaggccacc acttcaagaa ctctgtagca ccgcctacat
3901 acctcgctct gctaatcctg ttaccagtgg ctgctgccag tggcgataag tcgtgtctta
3961 ccgggttgga ctcaagacga tagttaccgg ataaggcgca gcggtcgggc tgaacggggg
4021 gttcgtgcac acagcccagc ttggagcgaa cgacctacac cgaactgaga tacctacagc
4081 gtgagctatg agaaagcgcc acgcttcccg aagggagaaa ggcggacagg tatccggtaa
4141 gcggcagggt cggaacagga gagcgcacga gggagcttcc agggggaaac gcctggtatc
4201 tttatagtcc tgtcgggttt cgccacctct gacttgagcg tcgatttttg tgatgctcgt
4261 caggggggcg gagcctatgg aaaaacgcca gcaacgcggc ctttttacgg ttcctggcct
4321 tttgctggcc ttttgctcac atgttctttc ctgcgttatc ccctgattct gtggataacc
4381 gtattaccgc ctttgagtga gctgataccg ctcgccgcag ccgaacgacc gagcgcagcg
4441 agtcagtgag cgaggaagcg gaagagcgcc tgatgcggta ttttctcctt acgcatctgt
```

FIG. 4, con't.

```
4501 gcggtatttc acaccgcata tggtgcactc tcagtacaat ctgctctgat gccgcatagt
4561 taagccagta tacactccgc tatcgctacg tgactgggtc atggctgcgc cccgacaccc
4621 gccaacaccc gctgacgcgc cctgacgggc ttgtctgctc ccggcatccg cttacagaca
4681 agctgtgacc gtctccggga gctgcatgtg tcagaggttt tcaccgtcat caccgaaacg
4741 cgcgaggcag cagatcaatt cgcgcgcgaa ggcgaagcgg catgcattta cgttgacacc
4801 atcgaatggt gcaaaacctt tcgcggtatg gcatgatagc gcccggaaga gagtcaattc
4861 agggtggtga atgtgaaacc agtaacgtta tacgatgtcg cagagtatgc cggtgtctct
4921 tatcagaccg tttcccgcgt ggtgaaccag gccagccacg tttctgcgaa aacgcgggaa
4981 aaagtggaag cggcgatggc ggagctgaat tacattccca accgcgtggc acaacaactg
5041 gcgggcaaac agtcgttgct gattggcgtt gccacctcca gtctggccct gcacgcgccg
5101 tcgcaaattg tcgcggcgat taaatctcgc gccgatcaac tgggtgccag cgtggtggtg
5161 tcgatggtag aacgaagcgg cgtcgaagcc tgtaaagcgg cggtgcacaa tcttctcgcg
5221 caacgcgtca gtgggctgat cattaactat ccgctggatg accaggatgc cattgctgtg
5281 gaagctgcct gcactaatgt tccggcgtta tttcttgatg tctctgacca gacacccatc
5341 aacagtatta ttttctccca tgaagacggt acgcgactgg gcgtggagca tctggtcgca
5401 ttgggtcacc agcaaatcgc gctgttagcg ggcccattaa gttctgtctc ggcgcgtctg
5461 cgtctggctg gctggcataa atatctcact cgcaatcaaa ttcagccgat agcggaacgg
5521 gaaggcgact ggagtgccat gtccggtttt caacaaacca tgcaaatgct gaatgagggc
5581 atcgttccca ctgcgatgct ggttgccaac gatcagatgg cgctgggcgc aatgcgcgcc
5641 attaccgagt ccgggctgcg cgttggtgcg gatatctcgg tagtgggata cgacgatacc
5701 gaagacagct catgttatat cccgccgtca accaccatca aacaggattt tcgcctgctg
5761 gggcaaacca gcgtggaccg cttgctgcaa ctctctcagg gccaggcggt gaagggcaat
5821 cagctgttgc ccgtctcact ggtgaaaaga aaaaccaccc tggcgcccaa tacgcaaacc
5881 gcctctcccc gcgcgttggc cgattcatta atgcagctgg cacgacaggt ttcccgactg
5941 gaaagcgggc agtgagcgca acgcaattaa tgtgagttag cgcgaattga tctg
```

FIG. 4, con't.

pTRC99a-YebF-FlAsH-6His (SEQ ID NO: 6)(SEQ ID NO: 5)

```
FEATURES             Location/Qualifiers
     source          1..4581
                     /organism="Cloning vector pTrc99A"
                     /mol_type="genomic DNA"
                     /db_xref="taxon:40992"
                     /lab_host="Escherichia coli"
                     /note="derived from pKK233-2"
     misc_feature    1..17
                     /note="derived from cloning vector pBR322"
     promoter        18..263
                     /note="trc promoter from pKK233-2"
                     /citation=[1]
     misc_feature    264..266
                     /note="NcoI/EcoRI linker"
     misc_feature    734..1158
                     /note="5S RNA, T1, T2, rrnB"
     misc_feature    1159..3337
                     /note="derived from cloning vector pBR322"
     misc_feature    3330..3345
                     /note="BglII linker"
     misc_feature    3338..3343
                     /note="BglII linker"
     misc_feature    3344..3350
                     /note="EcoRI linker"
     misc_feature    3351..3381
                     /note="derived from plasmid RP4"
     misc_feature    3382..4568
                     /note="lacI-q region"
     misc_feature    4569..4575
                     /note="EcoRI linker"
     misc_feature    4576..4581
                     /note="BglII linker"
     misc_feature    681..698
                     /note="6XHis" (SEQ ID NO: 6)
     misc_binding    645..680
                     /note="FlAsH"
     gene            291..644
                     /note="YebF"
ORIGIN
        1 gtttgacagc ttatcatcga ctgcacggtg caccaatgct tctggcgtca ggcagccatc
       61 ggaagctgtg gtatggctgt gcaggtcgta aatcactgca taattcgtgt cgctcaaggc
      121 gcactcccgt tctggataat gttttttgcg ccgacatcat aacggttctg gcaaatattc
      181 tgaaatgagc tgttgacaat taatcatccg gctcgtataa tgtgtggaat tgtgagcgga
      241 taacaatttc acacaggaaa cagaccATGG AATTCGAGCT CGAGAAAAAC ATGAAAAAAA
      301 GAGGGGCGTT TTTAGGGCTG TTGTTGGTTT CTGCCTGCGC ATCAGTTTTC GCTGCCAATA
      361 ATGAAACCAG CAAGTCGGTC ACTTTCCCAA AGTGTGAAGA TCTGGATGCT GCCGGAATTG
      421 CCGCGAGCGT AAAACGTGAT TATCAACAAA ATCGCGTGGC GCGTTGGGCA GATGATCAAA
      481 AAATTGTCGG TCAGGCCGAT CCCGTGGCTT GGGTCAGTTT GCAGGACATT CAGGGTAAAG
      541 ATGATAAATG GTCAGTACCG CTAACCGTGC GTGGTAAAAG TGCCGATATT CATTACCAGG
      601 TCAGCGTGGA CTGCAAAGCG GGAATGGCGG AATATCAGCG GCGTTTTCTG AACTGCTGCC
      641 CGGGCTGCTG CATGGAACCG CATCATCACC ATCACCACTA Atctagagtc gacctgcagg
      721 catgcaagct tggctgtttt ggcggatgag agaagatttt cagcctgata cagattaaat
      781 cagaacgcag aagcggtctg ataaaacaga atttgcctgg cggcagtagc gcggtggtcc
      841 cacctgaccc catgccgaac tcagaagtga aacgccgtag cgccgatggt agtgtggggt
      901 ctccccatgc gagagtaggg aactgccagg catcaaataa aacgaaaggc tcagtcgaaa
      961 gactgggcct ttcgttttat ctgttgtttg tcggtgaacg ctctcctgag taggacaaat
     1021 ccgccgggag cggatttgaa cgttgcgaag caacggcccg gagggtggcg ggcaggacgc
```

FIG. 4, con't.

1081 ccgccataaa ctgccaggca tcaaattaag cagaaggcca tcctgacgga tggccttttt
1141 gcgtttctac aaactctttt tgtttatttt tctaaataca ttcaaatatg tatccgctca
1201 tgagacaata accctgataa atgcttcaat aatattgaaa aaggaagagt atgagtattc
1261 aacatttccg tgtcgccctt attccctttt ttgcggcatt ttgccttcct gtttttgctc
1321 acccagaaac gctggtgaaa gtaaaagatg ctgaagatca gttgggtgca cgagtgggtt
1381 acatcgaact ggatctcaac agcggtaaga tccttgagag ttttcgcccc gaagaacgtt
1441 ttccaatgat gagcactttt aaagttctgc tatgtggcgc ggtattatcc cgtgttgacg
1501 ccgggcaaga gcaactcggt cgccgcatac actattctca gaatgacttg gttgagtact
1561 caccagtcac agaaaagcat cttacggatg gcatgacagt aagagaatta tgcagtgctg
1621 ccataaccat gagtgataac actgcggcca acttacttct gacaacgatc ggaggaccga
1681 aggagctaac cgcttttttg cacaacatgg gggatcatgt aactcgcctt gatcgttggg
1741 aaccggagct gaatgaagcc ataccaaacg acgagcgtga caccacgatg cctacagcaa
1801 tggcaacaac gttgcgcaaa ctattaactg gcgaactact tactctagct tcccggcaac
1861 aattaataga ctggatggag gcggataaag ttgcaggacc acttctgcgc tcggcccttc
1921 cggctggctg gtttattgct gataaatctg gagccggtga gcgtgggtct cgcggtatca
1981 ttgcagcact ggggccagat ggtaagccct cccgtatcgt agttatctac acgacgggga
2041 gtcaggcaac tatggatgaa cgaaatagac agatcgctga gataggtgcc tcactgatta
2101 agcattggta actgtcagac caagtttact catatatact ttagattgat ttaaaacttc
2161 atttttaatt taaaaggatc taggtgaaga tcctttttga taatctcatg accaaaatcc
2221 cttaacgtga gttttcgttc cactgagcgt cagaccccgt agaaaagatc aaaggatctt
2281 cttgagatcc tttttttctg cgcgtaatct gctgcttgca aacaaaaaaa ccaccgctac
2341 cagcggtggt ttgtttgccg gatcaagagc taccaactct ttttccgaag gtaactggct
2401 tcagcagagc gcagatacca aatactgtcc ttctagtgta gccgtagtta ggccaccact
2461 tcaagaactc tgtagcaccg cctacatacc tcgctctgct aatcctgtta ccagtggctg
2521 ctgccagtgg cgataagtcg tgtcttaccg ggttggactc aagacgatag ttaccggata
2581 aggcgcagcg gtcgggctga acggggggtt cgtgcacaca gcccagcttg gagcgaacga
2641 cctacaccga actgagatac ctacagcgtg agctatgaga aagcgccacg cttcccgaag
2701 ggagaaaggc ggacaggtat ccggtaagcg gcagggtcgg aacaggagag cgcacgaggg
2761 agcttccagg gggaaacgcc tggtatcttt atagtcctgt cgggtttcgc cacctctgac
2821 ttgagcgtcg atttttgtga tgctcgtcag gggggcggag cctatggaaa aacgccagca
2881 acgcggcctt tttacggttc ctggcctttt gctggccttt tgctcacatg ttctttcctg
2941 cgttatcccc tgattctgtg gataaccgta ttaccgcctt tgagtgagct gataccgctc
3001 gccgcagccg aacgaccgag cgcagcgagt cagtgagcga ggaagcggaa gagcgcctga
3061 tgcggtattt tctccttacg catctgtgcg gtatttcaca ccgcatatgg tgcactctca
3121 gtacaatctg ctctgatgcc gcatagttaa gccagtatac actccgctat cgctacgtga
3181 ctgggtcatg gctgcgcccc gacacccgcc aacacccgct gacgcgccct gacgggcttg
3241 tctgctcccg gcatccgctt acagacaagc tgtgaccgtc tccgggagct gcatgtgtca
3301 gaggttttca ccgtcatcac cgaaacgcgc gaggcagcag atcaattcgc gcgcgaaggc
3361 gaagcggcat gcatttacgt tgacaccatc gaatggtgca aaacctttcg cggtatggca
3421 tgatagcgcc cggaagagag tcaattcagg gtggtgaatg tgaaaccagt aacgttatac
3481 gatgtcgcag agtatgccgg tgtctcttat cagaccgttt cccgcgtggt gaaccaggcc
3541 agccacgttt ctgcgaaaac gcgggaaaaa gtggaagcgg cgatggcgga gctgaattac
3601 attcccaacc gcgtggcaca acaactggcg ggcaaacagt cgttgctgat tggcgttgcc
3661 acctccagtc tggccctgca cgcgccgtcg caaattgtcg cggcgattaa atctcgcgcc
3721 gatcaactgg gtgccagcgt ggtggtgtcg atggtagaac gaagcggcgt cgaagcctgt
3781 aaagcggcgg tgcacaatct tctcgcgcaa cgcgtcagtg ggctgatcat taactatccg
3841 ctggatgacc aggatgccat tgctgtggaa gctgcctgca ctaatgttcc ggcgttattt
3901 cttgatgtct ctgaccagac acccatcaac agtattattt tctcccatga agacggtacg
3961 cgactgggcg tggagcatct ggtcgcattg ggtcaccagc aaatcgcgct gttagcgggc
4021 ccattaagtt ctgtctcggc gcgtctgcgt ctggctggct ggcataaata tctcactcgc
4081 aatcaaattc agccgatagc ggaacgggaa ggcgactgga gtgccatgtc cggttttcaa
4141 caaaccatgc aaatgctgaa tgagggcatc gttcccactg cgatgctggt tgccaacgat
4201 cagatggcgc tgggcgcaat gcgcgccatt accgagtccg ggctgcgcgt tggtgcggat
4261 atctcggtag tgggatacga cgataccgaa gacagctcat gttatatccc gccgtcaacc
4321 accatcaaac aggattttcg cctgctgggg caaaccagcg tggaccgctt gctgcaactc
4381 tctcagggcc aggcggtgaa gggcaatcag ctgttgcccg tctcactggt gaaaagaaaa
4441 accaccctgg cgcccaatac gcaaaccgcc tctccccgcg cgttggccga ttcattaatg
4501 cagctggcac gacaggtttc ccgactggaa agcgggcagt gagcgcaacg caattaatgt
4561 gagttagcgc gaattgatct g

SEQUENCE LISTING

```
<160> NUMBER OF SEQ ID NOS: 9

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Lys Lys Arg Gly Ala Phe Leu Gly Leu Leu Leu Val Ser Ala Cys
1               5                   10                  15

Ala Ser Val Phe Ala Ala Asn Asn Glu Thr Ser Lys Ser Val Thr Phe
```

```
            20                  25                  30

Pro Lys Cys Glu Gly Leu Asp Ala Ala Gly Ile Ala Ala Ser Val Lys
        35                  40                  45

Arg Asp Tyr Gln Gln Asn Arg Val Ala Arg Trp Ala Asp Asp Gln Lys
    50                  55                  60

Ile Val Gly Gln Ala Asp Pro Val Ala Trp Val Ser Leu Gln Asp Ile
65                  70                  75                  80

Gln Gly Lys Asp Asp Lys Trp Ser Val Pro Leu Thr Val Arg Gly Lys
                85                  90                  95

Ser Ala Asp Ile His Tyr Gln Val Ser Val Asp Cys Lys Ala Gly Met
            100                 105                 110

Ala Glu Tyr Gln Arg Arg
        115


<210> SEQ ID NO 2
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

atgaaaaaaa gaggggcgtt tttagggctg ttgttggttt ctgcctgcgc atcagttttc     60

gctgccaata atgaaaccag caagtcggtc actttcccaa agtgtgaaga tctggatgct    120

gccggaattg ccgcgagcgt aaaacgtgat tatcaacaaa atcgcgtggc gcgttgggca    180

gatgatcaaa aaattgtcgg tcaggccgat cccgtggctt gggtcagttt gcaggacatt    240

cagggtaaag atgataaatg gtcagtaccg ctaaccgtgc gtggtaaaag tgccgatatt    300

cattaccagg tcagcgtgga ctgcaaagcg ggaatggcgg aatatcagcg gcgttaa       357


<210> SEQ ID NO 3
<211> LENGTH: 6120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

gtttgacagc ttatcatcga ctgcacggtg caccaatgct tctggcgtca ggcagccatc     60

ggaagctgtg gtatggctgt gcaggtcgta aatcactgca taattcgtgt cgctcaaggc    120

gcactcccgt tctggataat gttttttgcg ccgacatcat aacggttctg gcaaatattc    180

tgaaatgagc tgttgacaat taatcatccg gctcgtataa tgtgtggaat tgtgagcgga    240

taacaatttc acacaggaaa cagaccatgg aattcgagct cgagaaaaac atgaaaaaaa    300

gaggggcgtt tttagggctg ttgttggttt ctgcctgcgc atcagttttc gctgccaata    360

atgaaaccag caagtcggtc actttcccaa agtgtgaaga tctggatgct gccggaattg    420

ccgcgagcgt aaaacgtgat tatcaacaaa atcgcgtggc gcgttgggca gatgatcaaa    480

aaattgtcgg tcaggccgat cccgtggctt gggtcagttt gcaggacatt cagggtaaag    540

atgataaatg gtcagtaccg ctaaccgtgc gtggtaaaag tgccgatatt cattaccagg    600

tcagcgtgga ctgcaaagcg ggaatggcgg aatatcagcg gcgttctaga gatgtcgccc    660

cattgagcgt gcaaggcaac aagatcctgg cgaatggtca gccggcgagc ttcagcggta    720

tgagcctgtt ttggagcaat accgagtggg gtggcgagaa gtactataac gcgcaagttg    780
```

```
tttcctggtt gaaatcggat tggaacgcca agctggtccg cgcagcgatg ggtgttgagg    840
atgaaggcgg ttacctgacc gacccggcga ataaggatcg cgtgactcaa gtggtggacg    900
cagcgatcgc aaacgacatg tacgtgatca tcgactggca tagccataat gcacaccaat    960
atcagtctca ggccatcgcc ttctttcagg agatggctcg caagtatggt gcgaacaacc   1020
acgtgatcta tgaaatctac aatgagcctt tgcaggtgag ctggtctaac actatcaaac   1080
cgtatgcgca agcggtgatt gcggcgatcc gtgcgattga cccagacaat ctgattatcg   1140
tgggtacgcc gacctggagc caggatgtcg acgtcgcggc gaatgacccg attacgggtt   1200
accagaacat tgcgtatacc ctgcatttct atgcgggtac gcacggtcaa tacctgcgtg   1260
ataaggcaca gaccgcactg aatcgtggca ttgctctgtt tgtcaccgaa tggggctcgg   1320
ttaatgcgaa tggtgatggc gccgttgcta atagcgaaac caatgcttgg gtgagcttta   1380
tgaaaaccaa tcacatctcc aacgcgaact gggcactgaa tgacaaagtt gagggcgcaa   1440
gcgcattggt cccgggtgcc agcgcaaacg gcggctgggt taacagccaa ttgaccgcgt   1500
ccggcgctct ggccaaaagc atcatcagcg gctggccgag ctacaatacc agctccagca   1560
gcagcgcggt ttccagccag acgcaagtca gcagctcgtc ccaagccccg gtcgtgtcta   1620
gctctagcag cacggcgtcg agcgtggtta gctccgctgt cagcggccaa cagtgtaact   1680
ggtatggtac gttgtatcca ctgtgcagca cgaccacgaa cggttggggt tgggaaaaca   1740
acgcgtcgtg cattgcgcgt gcaacgtgca gcggtcagcc ggcaccgtgg ggtatcgtcg   1800
gcggtagcac cagcagccaa gcgtcctcca gcgtccgcag cagcagcagc tctctggtca   1860
gctccagccg tagcagcagc agcagctctg ttcagtctag cagcgcgcct tcgtcggtgg   1920
cgagcagcag cggcagcagc agcggccagt gcagctacac cgttaccaat cagtggagca   1980
acggttttac cgcatccatc cgtattgcga acaatggcac cagcccgatc aacggttgga   2040
atctgagctg gagctactct gacggtagcc gtgttaccaa ttcttggaac gcgaatgtgt   2100
ctggcaataa cccatacacc gcatctaacc tgggttggaa tggcagcatt caaccgggtc   2160
aagctgtgga gtttggcttt cagggcacca agaataacag cgctgcggct atcccgaccc   2220
tgagcggcaa cgtgtgcaac aaccatcatc accatcacca ctaaaagctt ggctgttttg   2280
gcggatgaga gaagattttc agcctgatac agattaaatc agaacgcaga agcggtctga   2340
taaaacagaa tttgcctggc ggcagtagcg cggtggtccc acctgacccc atgccgaact   2400
cagaagtgaa acgccgtagc gccgatggta gtgtggggtc tccccatgcg agagtaggga   2460
actgccaggc atcaaataaa acgaaaggct cagtcgaaag actgggcctt tcgttttatc   2520
tgttgtttgt cggtgaacgc tctcctgagt aggacaaatc cgccgggagc ggatttgaac   2580
gttgcgaagc aacggcccgg agggtggcgg gcaggacgcc cgccataaac tgccaggcat   2640
caaattaagc agaaggccat cctgacggat ggcctttttg cgtttctaca aactcttttt   2700
gtttattttt ctaaatacat tcaaatatgt atccgctcat gagacaataa ccctgataaa   2760
tgcttcaata atattgaaaa aggaagagta tgagtattca acatttccgt gtcgccctta   2820
ttcccttttt tgcggcattt tgccttcctg tttttgctca cccagaaacg ctggtgaaag   2880
taaaagatgc tgaagatcag ttgggtgcac gagtgggtta catcgaactg gatctcaaca   2940
gcggtaagat ccttgagagt tttcgccccg aagaacgttt tccaatgatg agcactttta   3000
aagttctgct atgtggcgcg gtattatccc gtgttgacgc cgggcaagag caactcggtc   3060
gccgcataca ctattctcag aatgacttgg ttgagtactc accagtcaca gaaaagcatc   3120
```

```
ttacggatgg catgacagta agagaattat gcagtgctgc cataaccatg agtgataaca   3180
ctgcggccaa cttacttctg acaacgatcg gaggaccgaa ggagctaacc gcttttttgc   3240
acaacatggg ggatcatgta actcgccttg atcgttggga accggagctg aatgaagcca   3300
taccaaacga cgagcgtgac accacgatgc ctacagcaat ggcaacaacg ttgcgcaaac   3360
tattaactgg cgaactactt actctagctt cccggcaaca attaatagac tggatggagg   3420
cggataaagt tgcaggacca cttctgcgct cggcccttcc ggctggctgg tttattgctg   3480
ataaatctgg agccggtgag cgtgggtctc gcggtatcat tgcagcactg gggccagatg   3540
gtaagccctc ccgtatcgta gttatctaca cgacggggag tcaggcaact atggatgaac   3600
gaaatagaca gatcgctgag ataggtgcct cactgattaa gcattggtaa ctgtcagacc   3660
aagtttactc atatatactt tagattgatt taaaacttca tttttaattt aaaaggatct   3720
aggtgaagat cctttttgat aatctcatga ccaaaatccc ttaacgtgag ttttcgttcc   3780
actgagcgtc agaccccgta gaaaagatca aaggatcttc ttgagatcct ttttttctgc   3840
gcgtaatctg ctgcttgcaa acaaaaaaac caccgctacc agcggtggtt tgtttgccgg   3900
atcaagagct accaactctt tttccgaagg taactggctt cagcagagcg cagataccaa   3960
atactgtcct tctagtgtag ccgtagttag gccaccactt caagaactct gtagcaccgc   4020
ctacatacct cgctctgcta atcctgttac cagtggctgc tgccagtggc gataagtcgt   4080
gtcttaccgg gttggactca agacgatagt taccggataa ggcgcagcgg tcgggctgaa   4140
cggggggttc gtgcacacag cccagcttgg agcgaacgac ctacaccgaa ctgagatacc   4200
tacagcgtga gctatgagaa agcgccacgc ttcccgaagg gagaaaggcg gacaggtatc   4260
cggtaagcgg cagggtcgga acaggagagc gcacgaggga gcttccaggg ggaaacgcct   4320
ggtatcttta tagtcctgtc gggtttcgcc acctctgact tgagcgtcga tttttgtgat   4380
gctcgtcagg ggggcggagc ctatggaaaa acgccagcaa cgcggccttt ttacggttcc   4440
tggccttttg ctggcctttt gctcacatgt tctttcctgc gttatcccct gattctgtgg   4500
ataaccgtat taccgccttt gagtgagctg ataccgctcg ccgcagccga acgaccgagc   4560
gcagcgagtc agtgagcgag gaagcggaag agcgcctgat gcggtatttt ctccttacgc   4620
atctgtgcgg tatttcacac cgcatatggt gcactctcag tacaatctgc tctgatgccg   4680
catagttaag ccagtataca ctccgctatc gctacgtgac tgggtcatgg ctgcgccccg   4740
acacccgcca acacccgctg acgcgccctg acgggcttgt ctgctcccgg catccgctta   4800
cagacaagct gtgaccgtct ccgggagctg catgtgtcag aggttttcac cgtcatcacc   4860
gaaacgcgcg aggcagcaga tcaattcgcg cgcgaaggcg aagcggcatg catttacgtt   4920
gacaccatcg aatggtgcaa aacctttcgc ggtatggcat gatagcgccc ggaagagagt   4980
caattcaggg tggtgaatgt gaaaccagta acgttatacg atgtcgcaga gtatgccggt   5040
gtctcttatc agaccgtttc ccgcgtggtg aaccaggcca gccacgtttc tgcgaaaacg   5100
cgggaaaaag tggaagcggc gatggcggag ctgaattaca ttcccaaccg cgtggcacaa   5160
caactggcgg gcaaacagtc gttgctgatt ggcgttgcca cctccagtct ggccctgcac   5220
gcgccgtcgc aaattgtcgc ggcgattaaa tctcgcgccg atcaactggg tgccagcgtg   5280
gtggtgtcga tggtagaacg aagcggcgtc gaagcctgta aagcggcggt gcacaatctt   5340
ctcgcgcaac gcgtcagtgg gctgatcatt aactatccgc tggatgacca ggatgccatt   5400
gctgtggaag ctgcctgcac taatgttccg gcgttatttc ttgatgtctc tgaccagaca   5460
cccatcaaca gtattatttt ctcccatgaa gacggtacgc gactgggcgt ggagcatctg   5520
```

```
gtcgcattgg gtcaccagca aatcgcgctg ttagcgggcc cattaagttc tgtctcggcg   5580

cgtctgcgtc tggctggctg gcataaatat ctcactcgca atcaaattca gccgatagcg   5640

gaacgggaag gcgactggag tgccatgtcc ggttttcaac aaaccatgca aatgctgaat   5700

gagggcatcg ttcccactgc gatgctggtt gccaacgatc agatggcgct gggcgcaatg   5760

cgcgccatta ccgagtccgg gctgcgcgtt ggtgcggata tctcggtagt gggatacgac   5820

gataccgaag acagctcatg ttatatcccg ccgtcaacca ccatcaaaca ggattttcgc   5880

ctgctggggc aaaccagcgt ggaccgcttg ctgcaactct ctcagggcca ggcggtgaag   5940

ggcaatcagc tgttgcccgt ctcactggtg aaaagaaaaa ccaccctggc gcccaatacg   6000

caaaccgcct ctccccgcgc gttggccgat tcattaatgc agctggcacg acaggtttcc   6060

cgactggaaa gcgggcagtg agcgcaacgc aattaatgtg agttagcgcg aattgatctg   6120
```

```
<210> SEQ ID NO 4
<211> LENGTH: 5994
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

gtttgacagc ttatcatcga ctgcacggtg caccaatgct tctggcgtca ggcagccatc     60

ggaagctgtg gtatggctgt gcaggtcgta aatcactgca taattcgtgt cgctcaaggc    120

gcactcccgt tctggataat gtttttttgcg ccgacatcat aacggttctg gcaaatattc   180

tgaaatgagc tgttgacaat taatcatccg gctcgtataa tgtgtggaat tgtgagcgga    240

taacaatttc acacaggaaa cagaccatgg aattcgagct cgagaaaaac atgaaaaaaa    300

gaggggcgtt tttagggctg ttgttggttt ctgcctgcgc atcagttttc gctgccaata    360

atgaaaccag caagtcggtc actttcccaa agtgtgaaga tctggatgct gccggaattg    420

ccgcgagcgt aaaacgtgat tatcaacaaa atcgcgtggc gcgttgggca gatgatcaaa    480

aaattgtcgg tcaggccgat cccgtggctt gggtcagttt gcaggacatt cagggtaaag    540

atgataaatg gtcagtaccg ctaaccgtgc gtggtaaaag tgccgatatt cattaccagg    600

tcagcgtgga ctgcaaagcg ggaatggcgg aatatcagcg gcgttttctg aactgctgcc    660

cgggctgctg catggaaccg catcatcacc atcaccacta atctagagtc gacctgcagg    720

catgcaagct tggctgtttt ggcggatgag agaagatttt cagcctgata cagattaaat    780

cagaacgcag aagcggtctg ataaaacaga atttgcctgg cggcagtagc gcggtggtcc    840

cacctgaccc catgccgaac tcagaagtga aacgccgtag cgccgatggt agtgtggggt    900

ctccccatgc gagagtaggg aactgccagg catcaaataa aacgaaaggc tcagtcgaaa    960

gactgggcct ttcgttttat ctgttgtttg tcggtgaacg ctctcctgag taggacaaat   1020

ccgccgggag cggatttgaa cgttgcgaag caacggcccg gagggtggcg ggcaggacgc   1080

ccgccataaa ctgccaggca tcaaattaag cagaaggcca tcctgacgga tggccttttt   1140

gcgtttctac aaactctttt tgtttatttt tctaaataca ttcaaatatg tatccgctca   1200

tgagacaata accctgataa atgcttcaat aatattgaaa aaggaagagt atgagtattc   1260

aacatttccg tgtcgccctt attccctttt ttgcggcatt ttgccttcct gtttttgctc   1320

acccagaaac gctggtgaaa gtaaaagatg ctgaagatca gttgggtgca cgagtgggtt   1380

acatcgaact ggatctcaac agcggtaaga tccttgagag ttttcgcccc gaagaacgtt   1440
```

```
ttccaatgat gagcactttt aaagttctgc tatgtggcgc ggtattatcc cgtgttgacg   1500
ccgggcaaga gcaactcggt cgccgcatac actattctca gaatgacttg gttgagtact   1560
caccagtcac agaaaagcat cttacggatg gcatgacagt aagagaatta tgcagtgctg   1620
ccataaccat gagtgataac actgcggcca acttacttct gacaacgatc ggaggaccga   1680
aggagctaac cgcttttttg cacaacatgg gggatcatgt aactcgcctt gatcgttggg   1740
aaccggagct gaatgaagcc ataccaaacg acgagcgtga caccacgatg cctacagcaa   1800
tggcaacaac gttgcgtaag aggttccaac tttcaccata atgaaataag atcactaccg   1860
ggcgtatttt ttgagttatc gagattttca ggagctaagg aagctaaaat ggagaaaaaa   1920
atcactggat ataccaccgt tgatatatcc caatggcatc gtaaagaaca ttttgaggca   1980
tttcagtcag ttgctcaatg tacctataac cagaccgttc agctggatat tacggccttt   2040
ttaaagaccg taaagaaaaa taagcacaag ttttatccgg cctttattca cattcttgcc   2100
cgcctgatga atgctcatcc ggaattccgt atggcaatga aagacggtga gctggtgata   2160
tgggatagtg ttcacccttg ttacaccgtt ttccatgagc aaactgaaac gttttcatcg   2220
ctctggagtg aataccacga cgatttccgg cagtttctac acatatattc gcaagatgtg   2280
gcgtgttacg gtgaaaacct ggcctatttc cctaaagggt ttattgagaa tatgtttttc   2340
gtctcagcca atccctgggt gagtttcacc agttttgatt taaacgtggc caatatggac   2400
aacttcttcg cccccgtttt caccatgggc aaatattata cgcaaggcga caaggtgctg   2460
atgccgctgg cgattcaggt tcatcatgcc gtctgtgatg gcttccatgt cggcagaatg   2520
cttaatgaat tacaacagta ctgcgatgag tggcagggcg gggcgtaatt tttttaaggc   2580
agttattggt gcccttaaac gcctggtgct acgcctgaat aagtgataat aagcggatga   2640
atggcagaaa ttcgaaagca aattcgaccc ggtcgtcggt tcagggcagg gtcgttaaat   2700
agccgcttat gtctattgct ggtttaccgg tttattgact accggaagca gtgtgaccgt   2760
gtgcttctca aatgcctgag gccagtttgc tcaggctctc cccgtggagg taataattga   2820
cgatatgatc atttattctg cctcccagag cctgataaaa acggttagcg cttcgttaat   2880
acagatgtag gtgttccaca gggtagccag cagcatcctg cgatgcagat ccggaacata   2940
atggtgcagg gcgcttgttt cggcgtgggt atggtggcag gccccgtggc cgggggactg   3000
ttgggcgctg ccggcacctg tcctacgagt tgcatgataa agaagacagt cataagtgcg   3060
gcgacgatag tcatgccccg cgcccaccgg aaggagctac cggacagcgg tgcggactgt   3120
tgtaactcag aataagaaat gaggccgctc atggcgttga ctctcagtca tagtatcgtg   3180
gtatcaccgg ttggttccac tctctgttgc gggcaacttc agcagcacgc aaactattaa   3240
ctggcgaact acttactcta gcttcccggc aacaattaat agactggatg gaggcggata   3300
aagttgcagg accacttctg cgctcggccc ttccggctgg ctggtttatt gctgataaat   3360
ctggagccgg tgagcgtggg tctcgcggta tcattgcagc actggggcca gatggtaagc   3420
cctcccgtat cgtagttatc tacacgacgg ggagtcaggc aactatggat gaacgaaata   3480
gacagatcgc tgagataggt gcctcactga ttaagcattg gtaactgtca gaccaagttt   3540
actcatatat actttagatt gatttaaaac ttcattttta atttaaaagg atctaggtga   3600
agatcctttt tgataatctc atgaccaaaa tcccttaacg tgagttttcg ttccactgag   3660
cgtcagaccc cgtagaaaag atcaaaggat cttcttgaga tccttttttt ctgcgcgtaa   3720
tctgctgctt gcaaacaaaa aaaccaccgc taccagcggt ggtttgtttg ccggatcaag   3780
```

agctaccaac tctttttccg aaggtaactg gcttcagcag agcgcagata ccaaatactg 3840
tccttctagt gtagccgtag ttaggccacc acttcaagaa ctctgtagca ccgcctacat 3900
acctcgctct gctaatcctg ttaccagtgg ctgctgccag tggcgataag tcgtgtctta 3960
ccgggttgga ctcaagacga tagttaccgg ataaggcgca gcggtcgggc tgaacggggg 4020
gttcgtgcac acagcccagc ttggagcgaa cgacctacac cgaactgaga tacctacagc 4080
gtgagctatg agaaagcgcc acgcttcccg aagggagaaa ggcggacagg tatccggtaa 4140
gcggcagggt cggaacagga gagcgcacga gggagcttcc agggggaaac gcctggtatc 4200
tttatagtcc tgtcgggttt cgccacctct gacttgagcg tcgatttttg tgatgctcgt 4260
caggggggcg gagcctatgg aaaaacgcca gcaacgcggc ctttttacgg ttcctggcct 4320
tttgctggcc ttttgctcac atgttctttc ctgcgttatc ccctgattct gtggataacc 4380
gtattaccgc ctttgagtga gctgataccg ctcgccgcag ccgaacgacc gagcgcagcg 4440
agtcagtgag cgaggaagcg gaagagcgcc tgatgcggta ttttctcctt acgcatctgt 4500
gcggtatttc acaccgcata tggtgcactc tcagtacaat ctgctctgat gccgcatagt 4560
taagccagta tacactccgc tatcgctacg tgactgggtc atggctgcgc cccgacaccc 4620
gccaacaccc gctgacgcgc cctgacgggc ttgtctgctc ccggcatccg cttacagaca 4680
agctgtgacc gtctccggga gctgcatgtg tcagaggttt tcaccgtcat caccgaaacg 4740
cgcgaggcag cagatcaatt cgcgcgcgaa ggcgaagcgg catgcattta cgttgacacc 4800
atcgaatggt gcaaaacctt tcgcggtatg gcatgatagc gcccggaaga gagtcaattc 4860
agggtggtga atgtgaaacc agtaacgtta tacgatgtcg cagagtatgc cggtgtctct 4920
tatcagaccg tttcccgcgt ggtgaaccag gccagccacg tttctgcgaa aacgcgggaa 4980
aaagtggaag cggcgatggc ggagctgaat tacattccca accgcgtggc acaacaactg 5040
gcgggcaaac agtcgttgct gattggcgtt gccacctcca gtctggccct gcacgcgccg 5100
tcgcaaattg tcgcggcgat taaatctcgc gccgatcaac tgggtgccag cgtggtggtg 5160
tcgatggtag aacgaagcgg cgtcgaagcc tgtaaagcgg cggtgcacaa tcttctcgcg 5220
caacgcgtca gtgggctgat cattaactat ccgctggatg accaggatgc cattgctgtg 5280
gaagctgcct gcactaatgt tccggcgtta tttcttgatg tctctgacca gacacccatc 5340
aacagtatta ttttctccca tgaagacggt acgcgactgg gcgtggagca tctggtcgca 5400
ttgggtcacc agcaaatcgc gctgttagcg ggcccattaa gttctgtctc ggcgcgtctg 5460
cgtctggctg gctggcataa atatctcact cgcaatcaaa ttcagccgat agcggaacgg 5520
gaaggcgact ggagtgccat gtccggtttt caacaaacca tgcaaatgct gaatgagggc 5580
atcgttccca ctgcgatgct ggttgccaac gatcagatgg cgctgggcgc aatgcgcgcc 5640
attaccgagt ccgggctgcg cgttggtgcg gatatctcgg tagtgggata cgacgatacc 5700
gaagacagct catgttatat cccgccgtca accaccatca aacaggattt tcgcctgctg 5760
gggcaaacca gcgtggaccg cttgctgcaa ctctctcagg gccaggcggt gaagggcaat 5820
cagctgttgc ccgtctcact ggtgaaaaga aaaaccaccc tggcgcccaa tacgcaaacc 5880
gcctctcccc gcgcgttggc cgattcatta atgcagctgg cacgacaggt ttcccgactg 5940
gaaagcgggc agtgagcgca acgcaattaa tgtgagttag cgcgaattga tctg 5994

<210> SEQ ID NO 5
<211> LENGTH: 4581
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
gtttgacagc ttatcatcga ctgcacggtg caccaatgct tctggcgtca ggcagccatc     60
ggaagctgtg gtatggctgt gcaggtcgta aatcactgca taattcgtgt cgctcaaggc    120
gcactcccgt tctggataat gtttttgcg ccgacatcat aacggttctg gcaaatattc     180
tgaaatgagc tgttgacaat taatcatccg gctcgtataa tgtgtggaat tgtgagcgga    240
taacaatttc acacaggaaa cagaccatgg aattcgagct cgagaaaaac atgaaaaaaa    300
gaggggcgtt tttagggctg ttgttggttt ctgcctgcgc atcagttttc gctgccaata    360
atgaaaccag caagtcggtc actttcccaa agtgtgaaga tctggatgct gccggaattg    420
ccgcgagcgt aaaacgtgat tatcaacaaa atcgcgtggc gcgttgggca gatgatcaaa    480
aaattgtcgg tcaggccgat cccgtggctt gggtcagttt gcaggacatt cagggtaaag    540
atgataaatg gtcagtaccg ctaaccgtgc gtggtaaaag tgccgatatt cattaccagg    600
tcagcgtgga ctgcaaagcg ggaatggcgg aatatcagcg gcgttttctg aactgctgcc    660
cgggctgctg catggaaccg catcatcacc atcaccacta atctagagtc gacctgcagg    720
catgcaagct tggctgtttt ggcggatgag agaagatttt cagcctgata cagattaaat    780
cagaacgcag aagcggtctg ataaaacaga atttgcctgg cggcagtagc gcggtggtcc    840
cacctgaccc catgccgaac tcagaagtga aacgccgtag cgccgatggt agtgtggggt    900
ctccccatgc gagagtaggg aactgccagg catcaaataa aacgaaaggc tcagtcgaaa    960
gactgggcct ttcgttttat ctgttgtttg tcggtgaacg ctctcctgag taggacaaat   1020
ccgccgggag cggatttgaa cgttgcgaag caacggcccg gagggtggcg ggcaggacgc   1080
ccgccataaa ctgccaggca tcaaattaag cagaaggcca tcctgacgga tggccttttt   1140
gcgtttctac aaactctttt tgtttatttt tctaaataca ttcaaatatg tatccgctca   1200
tgagacaata accctgataa atgcttcaat aatattgaaa aaggaagagt atgagtattc   1260
aacatttccg tgtcgccctt attccctttt ttgcggcatt ttgccttcct gtttttgctc   1320
acccagaaac gctggtgaaa gtaaaagatg ctgaagatca gttgggtgca cgagtgggtt   1380
acatcgaact ggatctcaac agcggtaaga tccttgagag ttttcgcccc gaagaacgtt   1440
ttccaatgat gagcactttt aaagttctgc tatgtggcgc ggtattatcc cgtgttgacg   1500
ccgggcaaga gcaactcggt cgccgcatac actattctca gaatgacttg gttgagtact   1560
caccagtcac agaaaagcat cttacggatg gcatgacagt aagagaatta tgcagtgctg   1620
ccataaccat gagtgataac actgcggcca acttacttct gacaacgatc ggaggaccga   1680
aggagctaac cgcttttttg cacaacatgg gggatcatgt aactcgcctt gatcgttggg   1740
aaccggagct gaatgaagcc ataccaaacg acgagcgtga caccacgatg cctacagcaa   1800
tggcaacaac gttgcgcaaa ctattaactg gcgaactact tactctagct tcccggcaac   1860
aattaataga ctggatggag gcggataaag ttgcaggacc acttctgcgc tcggcccttc   1920
cggctggctg gtttattgct gataaatctg gagccggtga gcgtgggtct cgcggtatca   1980
ttgcagcact ggggccagat ggtaagccct cccgtatcgt agttatctac acgacgggga   2040
gtcaggcaac tatggatgaa cgaaatagac agatcgctga gataggtgcc tcactgatta   2100
agcattggta actgtcagac caagtttact catatatact ttagattgat ttaaaacttc   2160
atttttaatt taaaaggatc taggtgaaga tcctttttga taatctcatg accaaaatcc   2220
```

-continued

```
cttaacgtga gttttcgttc cactgagcgt cagaccccgt agaaaagatc aaaggatctt   2280
cttgagatcc tttttttctg cgcgtaatct gctgcttgca aacaaaaaaa ccaccgctac   2340
cagcggtggt ttgtttgccg gatcaagagc taccaactct ttttccgaag gtaactggct   2400
tcagcagagc gcagatacca aatactgtcc ttctagtgta gccgtagtta ggccaccact   2460
tcaagaactc tgtagcaccg cctacatacc tcgctctgct aatcctgtta ccagtggctg   2520
ctgccagtgg cgataagtcg tgtcttaccg ggttggactc aagacgatag ttaccggata   2580
aggcgcagcg gtcgggctga acggggggtt cgtgcacaca gcccagcttg gagcgaacga   2640
cctacaccga actgagatac ctacagcgtg agctatgaga aagcgccacg cttcccgaag   2700
ggagaaaggc ggacaggtat ccggtaagcg gcagggtcgg aacaggagag cgcacgaggg   2760
agcttccagg gggaaacgcc tggtatcttt atagtcctgt cgggtttcgc cacctctgac   2820
ttgagcgtcg atttttgtga tgctcgtcag gggggcggag cctatggaaa aacgccagca   2880
acgcggcctt tttacggttc ctggcctttt gctggccttt tgctcacatg ttctttcctg   2940
cgttatcccc tgattctgtg gataaccgta ttaccgcctt tgagtgagct gataccgctc   3000
gccgcagccg aacgaccgag cgcagcgagt cagtgagcga ggaagcggaa gagcgcctga   3060
tgcggtattt tctccttacg catctgtgcg gtatttcaca ccgcatatgg tgcactctca   3120
gtacaatctg ctctgatgcc gcatagttaa gccagtatac actccgctat cgctacgtga   3180
ctgggtcatg gctgcgcccc gacacccgcc aacacccgct gacgcgccct gacgggcttg   3240
tctgctcccg gcatccgctt acagacaagc tgtgaccgtc tccgggagct gcatgtgtca   3300
gaggttttca ccgtcatcac cgaaacgcgc gaggcagcag atcaattcgc gcgcgaaggc   3360
gaagcggcat gcatttacgt tgacaccatc gaatggtgca aaacctttcg cggtatggca   3420
tgatagcgcc cggaagagag tcaattcagg gtggtgaatg tgaaaccagt aacgttatac   3480
gatgtcgcag agtatgccgg tgtctcttat cagaccgttt cccgcgtggt gaaccaggcc   3540
agccacgttt ctgcgaaaac gcgggaaaaa gtggaagcgg cgatggcgga gctgaattac   3600
attcccaacc gcgtggcaca acaactggcg ggcaaacagt cgttgctgat tggcgttgcc   3660
acctccagtc tggccctgca cgcgccgtcg caaattgtcg cggcgattaa atctcgcgcc   3720
gatcaactgg gtgccagcgt ggtggtgtcg atggtagaac gaagcggcgt cgaagcctgt   3780
aaagcggcgg tgcacaatct tctcgcgcaa cgcgtcagtg ggctgatcat taactatccg   3840
ctggatgacc aggatgccat tgctgtggaa gctgcctgca ctaatgttcc ggcgttattt   3900
cttgatgtct ctgaccagac acccatcaac agtattattt tctcccatga agacggtacg   3960
cgactgggcg tggagcatct ggtcgcattg ggtcaccagc aaatcgcgct gttagcgggc   4020
ccattaagtt ctgtctcggc gcgtctgcgt ctggctggct ggcataaata tctcactcgc   4080
aatcaaattc agccgatagc ggaacgggaa ggcgactgga gtgccatgtc cggttttcaa   4140
caaaccatgc aaatgctgaa tgagggcatc gttcccactg cgatgctggt tgccaacgat   4200
cagatggcgc tgggcgcaat gcgcgccatt accgagtccg ggctgcgcgt tggtgcggat   4260
atctcggtag tgggatacga cgataccgaa gacagctcat gttatatccc gccgtcaacc   4320
accatcaaac aggattttcg cctgctgggg caaaccagcg tggaccgctt gctgcaactc   4380
tctcagggcc aggcggtgaa gggcaatcag ctgttgcccg tctcactggt gaaaagaaaa   4440
accaccctgg cgcccaatac gcaaaccgcc tctccccgcg cgttggccga ttcattaatg   4500
cagctggcac gacaggtttc ccgactggaa agcgggcagt gagcgcaacg caattaatgt   4560
```

```
gagttagcgc gaattgatct g                                               4581


<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 6

His His His His His His
1               5


<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Cys Pro Gly Cys Cys
1               5


<210> SEQ ID NO 8
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Thr Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205
```

```
Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285


<210> SEQ ID NO 9
<211> LENGTH: 319
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Glu Leu Asn Tyr Ile Pro Asn Arg Val Ala Gln Gln Leu Ala
1               5                   10                  15

Gly Lys Gln Ser Leu Leu Ile Gly Val Ala Thr Ser Ser Leu Ala Leu
            20                  25                  30

His Ala Pro Ser Gln Ile Val Ala Ala Ile Lys Ser Arg Ala Asp Gln
        35                  40                  45

Leu Gly Ala Ser Val Val Val Ser Met Val Glu Arg Ser Gly Val Glu
    50                  55                  60

Ala Cys Lys Ala Ala Val His Asn Leu Leu Ala Gln Arg Val Ser Gly
65                  70                  75                  80

Leu Ile Ile Asn Tyr Pro Leu Asp Asp Gln Asp Ala Ile Ala Val Glu
                85                  90                  95

Ala Ala Cys Thr Asn Val Pro Ala Leu Phe Leu Asp Val Ser Asp Gln
            100                 105                 110

Thr Pro Ile Asn Ser Ile Ile Phe Ser His Glu Asp Gly Thr Arg Leu
        115                 120                 125

Gly Val Glu His Leu Val Ala Leu Gly His Gln Gln Ile Ala Leu Leu
    130                 135                 140

Ala Gly Pro Leu Ser Ser Val Ser Ala Arg Leu Arg Leu Ala Gly Trp
145                 150                 155                 160

His Lys Tyr Leu Thr Arg Asn Gln Ile Gln Pro Ile Ala Glu Arg Glu
                165                 170                 175

Gly Asp Trp Ser Ala Met Ser Gly Phe Gln Gln Thr Met Gln Met Leu
            180                 185                 190

Asn Glu Gly Ile Val Pro Thr Ala Met Leu Val Ala Asn Asp Gln Met
        195                 200                 205

Ala Leu Gly Ala Met Arg Ala Ile Thr Glu Ser Gly Leu Arg Val Gly
    210                 215                 220

Ala Asp Ile Ser Val Val Gly Tyr Asp Asp Thr Glu Asp Ser Ser Cys
225                 230                 235                 240

Tyr Ile Pro Pro Ser Thr Thr Ile Lys Gln Asp Phe Arg Leu Leu Gly
                245                 250                 255

Gln Thr Ser Val Asp Arg Leu Leu Gln Leu Ser Gln Gly Gln Ala Val
            260                 265                 270

Lys Gly Asn Gln Leu Leu Pro Val Ser Leu Val Lys Arg Lys Thr Thr
```

-continued

```
        275                 280                 285

Leu Ala Pro Asn Thr Gln Thr Ala Ser Pro Arg Ala Leu Ala Asp Ser
    290                 295                 300

Leu Met Gln Leu Ala Arg Gln Val Ser Arg Leu Glu Ser Gly Gln
305                 310                 315
```

SYSTEMS AND METHODS FOR THE SECRETION OF RECOMBINANT PROTEINS IN GRAM NEGATIVE BACTERIA

CROSS REFERENCE TO RELATED APPLICATIONS

The present application claims priority to U.S. Provisional Application Ser. No. 61/369,188, filed Jul. 30, 2010, the entire disclosure of which is hereby incorporated by reference.

STATEMENT OF GOVERNMENT SUPPORT

This invention was made with government support under DE-FC02-07ER64494 awarded by the U.S. Department of Energy. The government has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 12, 2011, is named 32261227.txt and is 30,272 bytes in size.

TECHNICAL FIELD

The present disclosure relates generally to systems and methods for producing recombinant proteins by secreting the recombinant proteins to the extracellular growth medium of a gram-negative bacteria.

BACKGROUND

The following discussion of the background is merely provided to aid the reader in understanding the invention and is not admitted to describe or constitute prior art.

Prokaryotes have been widely used for the production of recombinant proteins. Controlled expression of the desired polypeptide or protein is accomplished by coupling the gene encoding the protein through recombinant DNA techniques behind a promoter, the activity of which can be regulated by external factors. This expression construct is carried on a vector, most often a plasmid. Introduction of the plasmid carrying the expression construct into a host bacterium and culturing that organism in the presence of compounds which activate the promoter results in expression of the desired protein. In this way, large quantities of the desired protein can be produced.

*E. coli* is the most commonly used prokaryote for protein production. A variety of plasmid vectors have been developed for use in *E. coli*, which employ several different types of promoters, selectable markers, and origins of replication. In the most common arrangement, the expressed protein accumulates in the cytoplasm. While this approach is useful for some proteins, not all proteins can be accumulated in the cytoplasm in an active state. Often, when the desired protein is produced at high levels, it may be toxic to the host cell, or accumulate as an insoluble particle known as an inclusion body. Proteins which accumulate as inclusion bodies are difficult to recover in an active form. In such cases, it may be desirable to engineer the protein so that it is secreted from the cell.

*E. coli* and other gram-negative bacteria are generally considered poor hosts for secreted protein production. There are no well-understood secretory pathways in *E. coli* to transport heterologous proteins to the extracellular environment. The recent discovery of YebF-mediated secretion (*Nat. Biotechnol.* 2006. 24(1):100-4) is the first report of a native *E. coli* system capable of secreting both the native protein, YebF, and translational fusions to YebF. However, the expression level of YebF fusion proteins is typically low.

SUMMARY

The present disclosure is based on the discovery of *E. coli* mutations that substantially increase the amount of recombinant protein secreted from cells compared to wild-type *E. coli.*

In one aspect, the present disclosure provides a recombinant bacterium comprising a mutant bacterium that has been transformed with a recombinant vector comprising a first DNA sequence encoding a signal peptide or secretory protein operatively linked to a second DNA sequence encoding a heterologous protein, wherein the mutant bacterium comprises mutations in at least one gene selected from the group consisting of: ompR, envZ, nlpD, entC, entE, yebE, yihF, yebG, mzrA, ftsK, tnaA, ompC, and ompF or homologs thereof.

In one embodiment, the bacterium is a gram negative bacterium. In one embodiment, the bacterium is selected from the group consisting of *Escherichia, Salmonella, Yersinia*, and *Shigella*. In one embodiment, both the NlpD and EnvZ gene products are not expressed or are rendered non-functional. In one embodiment, both the NlpD and OmpR gene products are not expressed or are rendered non-functional. In one embodiment, the NlpD and YihF gene products are not expressed or are rendered non-functional. In one embodiment, the secretory protein is YebF.

In one aspect, the present disclosure provides an expression system for secreting a recombinant protein into a culture medium, the system comprising: (a) a mutant *E. coli* bacterium, wherein at least one gene product selected from the group consisting of OmpR, EnvZ, NlpD, EntC, EntE, YebE, YihF, YebG, MzrA, FtsK, TnaA, OmpC, and OmpF is not expressed or is rendered non-functional; and (b) a recombinant vector comprising a first DNA sequence encoding a signal peptide or secretory protein operatively linked to a second DNA sequence encoding a heterologous protein.

In one embodiment, both the NlpD and EnvZ gene products are not expressed or are rendered non-functional. In one embodiment, both the NlpD and OmpR gene products are not expressed or are rendered non-functional. In one embodiment, the NlpD and YihF gene products are not expressed or are rendered non-functional. In one embodiment, at least one gene product is not expressed or is rendered non-functional by deleting all or part of the gene encoding the gene product. In one embodiment, the at least one gene product is not expressed or is rendered non-functional by way of alteration of a promoter control sequence. In one embodiment, the promoter control sequence is altered by incorporation of an inducible promoter sequence element. In one embodiment, the promoter control sequence is altered by the incorporation of a repressor promoter sequence element. In one embodiment, the promoter control sequence is altered so as to provide a non-functional promoter control sequence.

In one embodiment, the secretory protein is YebF. In one embodiment, the signal peptide is capable of mediating transport of a protein to the periplasmic space. In one embodiment, the signal peptide is associated with the SEC, TAT, or SRP export pathway.

In one embodiment, the heterologous protein that is secreted is biologically active. In one embodiment, the heterologous protein is selected from the group consisting of: a cellulase, a protease, a lipase, a cutinase, an amylase, a galactosidase, a pullulanase, a glucose isomerase, a protein disuphide isomerase, a cyclodextrin gluconotransferase, a phytase, a glucose oxidase, a glucosyl transferase, laccase, bilirubin oxidase, a xylanase, an antigenic microbial or protozoan protein, a bacterial protein toxin, a viral protein, and a pharmaceutical. In one embodiment, the heterologous protein is selected from the group consisting of an immunoglobulin light chain, an immunoglobulin heavy chain, an immunoglobulin light chain fragment or an immunoglobulin heavy chain fragment.

In one embodiment, the expression of both DNA sequences is under the control of an inducible promoter. In one embodiment, the inducible promoter is a lac promoter.

In one embodiment, the at least one gene product selected from the group consisting of OmpR, EnvZ, NlpD, EntC, EntE, YebE, YihF, YebG, MzrA, FtsK, TnaA, OmpC, and OmpF is not expressed or is rendered non-functional by substitution, deletion, or insertion of one or more nucleotides in the gene encoding the at least one gene product.

In another aspect, the present disclosure provides a method for producing a recombinant protein comprising: (a) culturing an *E. coli* bacterium under conditions in which the bacterium secretes a heterologous protein into a culture medium, wherein the *E. coli* bacterium comprises: (i) a mutant *E. coli* bacterium, wherein at least one gene product selected from the group consisting of OmpR, EnvZ, NlpD, EntC, EntE, YebE, YihF, YebG, MzrA, FtsK, TnaA, OmpC, and OmpF is not expressed or is rendered non-functional; and (ii) a recombinant vector comprising a first DNA sequence encoding a signal peptide or carrier protein operatively linked to a second DNA sequence encoding a heterologous protein, and (b) isolating the secreted protein from the culture medium. In one embodiment, the method further comprises the step of purifying the secreted protein.

In another aspect, the present disclosure provides a method for producing a heterologous protein comprising: (a) transforming a host cell with a recombinant vector, wherein the host cell is a mutant *E. coli* bacterium, wherein at least one gene product selected from the group consisting of OmpR, EnvZ, NlpD, EntC, EntE, YebE, YihF, YebG, MzrA, FtsK, TnaA, OmpC, and OmpF is not expressed or is rendered non-functional, and wherein the recombinant vector comprises a first DNA sequence encoding a signal peptide or carrier protein operatively linked to a second DNA sequence encoding a heterologous protein; (b) culturing the host cell under conditions in which the bacterium secretes the heterologous protein into the culture medium; and (c) isolating the secreted protein from the culture medium.

BRIEF DESCRIPTION OF THE FIGURES

FIG. 4 shows the plasmid maps of the plasmids described in the examples.

DETAILED DESCRIPTION

Figure 1:
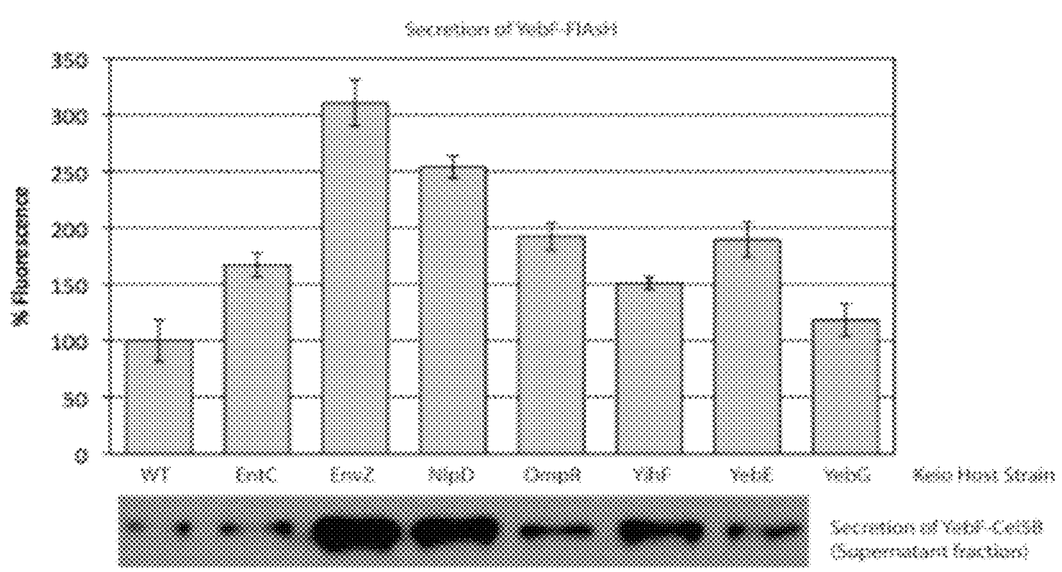
FIG. 1 is a graph showing improved protein secretion in mutant strains. The Keio host strain indicates what gene has been deleted from strain BW25113 ΔdsbA. WT indicates the wild-type background (*E. coli* BW25113 ΔdsbA). The upper graph shows the relative fluorescence from FlAsH-tagged YebF. Below that are the results of Western blots of secreted YebF-6×His-cellulase ("6×His" disclosed as SEQ ID NO: 6) fusion proteins.

The present disclosure relates inter alia to a recombinant bacterium that has been mutated in one or more genes that affect a YebF-mediated protein secretory pathway. The mutants exhibit increased secretion of YebF fusion proteins compared to wild-type *E. coli*. The mutants include bacteria containing mutations in at least one gene selected from the group consisting of: ompR, envZ, nlpD, entC, entE, YebE, yihF, yebG, mzrA, ftsK, tnaA, ompC, and ompF or homologs thereof.

In practicing the present invention, many conventional techniques in molecular biology, protein biochemistry, cell biology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); Perbal, *A Practical Guide to Molecular Cloning*; the series, *Meth. Enzymol*., (Academic Press, Inc., 1984); and *Meth. Enzymol*., Vols. 154 and 155, Wu & Grossman, and Wu, Eds., respectively.

As used in this specification and the appended claims, the singular forms "a", "an" and "the" include plural referents unless the content clearly dictates otherwise. For example, reference to "a cell" includes a combination of two or more cells, and the like.

As used herein, the term "expression vector" refers to a recombinant DNA molecule containing the appropriate control nucleotide sequences (e.g., promoters, enhancers, repressors, operator sequences and ribosome binding sites) necessary for the expression of an operably linked nucleotide sequence in a particular host cell. By "operably linked/linking" or "in operable combination" is meant that the nucleotide sequence is positioned relative to the control nucleotide sequences to initiate, regulate or otherwise direct transcription and/or the synthesis of the desired protein molecule. The expression vector may be self-replicating, such as a plasmid, and may therefore carry a replication site, or it may be a vector that integrates into a host chromosome either randomly or at a targeted site. The expression vector may contain a gene as a selectable marker for providing phenotypic selection in transformed cells. The expression vector may also contain sequences that are useful for the control of translation.

As used herein, a "fusion" protein is a recombinant protein comprising regions derived from at least two different proteins. The term "fusion protein" as used herein refers to a protein molecule in which a heterologous protein of interest is fused to secretory protein or a signal peptide, such as YebF. "Fused", in one context means that nucleic acid encoding the secretory protein or signal peptide is joined in frame to the nucleic acid encoding the heterologous protein interest, to provide for a single amino acid chain when transcription and translation occur. In another context, "fused" may also be a reference to the joining of a recombinant protein of interest to the secretory protein or signal peptide, such as YebF.

As used herein, "heterologous" refers to DNA, RNA, or protein that does not occur naturally as part of the organism in which it is present or which is found in a location or locations in the genome that differ from that in which it occurs in nature. It is DNA, RNA, or protein that is not endogenous to the cell and has been artificially introduced into the cell. Examples of heterologous DNA include, but are not limited to, DNA that encodes a cellulase. The heterologous DNA need not be expressed and may be introduced in a manner such that it is integrated into the host cell genome or is maintained episomally.

As used herein, the term "homolog" refers to any gene that is related to a reference gene by descent from a common ancestral DNA sequence. The term "ortholog" refers to homologs in different species that evolved from a common ancestral gene by speciation. Typically, orthologs retain the same or similar function despite differences in their primary structure (mutations). The term "paralog" refers to homologs in the same species that evolved by genetic duplication of a common ancestral gene. In many cases, paralogs exhibit related (but not always identical functions). As used herein, the term homolog encompasses both orthologs and paralogs. To the extent that a particular species has evolved multiple related genes from an ancestral DNA sequence shared with another species, the term ortholog can encompass the term paralog.

As used herein, the terms "identical" or percent "identity", when used in the context of two or more nucleic acids or polypeptide sequences, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." This term also refers to, or can be applied to, the complement of a test sequence. The term also includes sequences that have deletions and/or additions, as well as those that have substitutions. As described below, the preferred algorithms can account for gaps and the like. Suitably, identity exists over a region that is at least about 25 amino acids or nucleotides in length, or more preferably over a region that is 50-100 amino acids or nucleotides in length.

As used herein, the term "mutant" of a gene refers to a gene which has been altered, either naturally or artificially, changing the base sequence of the gene. The change in the base sequence may be of several different types, including changes of one or more bases for different bases, deletions, and/or insertions, such as by a transposon. By contrast, a normal form of a gene (wild type) is a form commonly found in natural populations of an organism. Commonly a single form of a gene will predominate in natural populations. In some embodiments, a mutant gene will be altered such that the product of that gene is not expressed, expressed at reduced or increased levels compared to wild type, or is rendered non-functional.

As used herein, "periplasm" refers to a gel-like region between the outer surface of the cytoplasmic membrane and the inner surface of the lipopolysaccharide layer of gram-negative bacteria.

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. The term polynucleotide also includes DNAs or RNAs containing one or more modified bases and DNAs or RNAs with backbones modified for stability or for other reasons.

As used herein, the terms "polypeptide", "peptide" and "protein" are used interchangeably herein to mean a polymer comprising two or more amino acids joined to each other by peptide bonds or modified peptide bonds. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, a "promoter" or "promoter region" refers to a portion of DNA that controls transcription of the DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, e.g., recombinant cells express genes that are not found within the native (non-recombinant) form of the cell or express native genes that are otherwise abnormally expressed, under expressed or not expressed at all.

As used herein, "secretion" refers to the excretion of the recombinant protein that is expressed in a bacterium to the periplasm or extracellular medium.

As used herein, "YebF" refers to an extracellular protein of *E. coli* with no known function having the amino acid sequence of SEQ ID NO:1 or biologically-active variants thereof. "yebF" is a reference to a nucleic acid or nucleotide sequence encoding SEQ ID NO: 1 or biologically-active variants thereof. In one embodiment, yebF has the sequence of SEQ ID NO:2.

Bacterial Strains and Mutants

Disclosed herein are modified bacteria useful for the production of secreted proteins. Modified bacteria may include bacteria with an improved (increased) ability to secrete proteins into the culture media, as compared to the similar, but non-modified (non-mutated) bacteria. An increase in the ability to secrete proteins includes, in various embodiments, about a 5%, 10%, 20%, 50%, 75%, 90%, 100%, 125%, or more increase in the amount of protein secreted into the medium compared to a similar, but non-modified (non-mutated) bacteria.

In one aspect, the present disclosure relates to genetically-modified *E. coli* bacteria containing a mutation in at least one gene which inhibits the YebF secretory pathway. In some embodiments, the mutation is in one or more genes selected from ompR, envZ, nlpD, entC, entE, yebE, yihF, yebG, mzrA, ftsK, tnaA, ompC, and ompF. In one embodiment, the genetically modified bacterium contains a single mutation in the ompR, envZ, nlpD, entC, entE, yebE, yihF, yebG, mzrA, ftsK, tnaA, ompC, or ompF gene. In one embodiment, the genetically modified bacterium contains a single mutation in the nlpD gene. In one embodiment, the genetically modified bacterium is a double mutant containing mutations in two genes selected from ompR, envZ, nlpD, entC, entE, yebE, yihF, yebG, mzrA, ftsK, tnaA, ompC, and ompF. In one embodiment, the genetically modified bacterium is a double mutant containing mutations in the nlpD and ompR genes. In one embodiment, the genetically modified bacterium is a double mutant containing mutations in the nlpD and envZ genes. In one embodiment, the genetically modified bacterium is a triple mutant containing mutations in three genes selected from ompR, envZ, nlpD, entC, entE, yebE, yihF, yebG, mzrA, ftsK, tnaA, ompC, and ompF. In one embodiment, the genetically modified bacterium contains mutations in four genes selected from ompR, envZ, nlpD, entC, entE, yebE, yihF, yebG, mzrA, ftsK, tnaA, ompC, and ompF. In one embodiment, the genetically modified bacterium contains mutations in five genes selected from ompR, envZ, nlpD, entC, entE, yebE, yihF, yebG, mzrA, ftsK, tnaA, ompC, and ompF. In one embodiment, the genetically modified bacterium contains mutations in the ompR, nlpD, entC, entE, yebE, and yihF genes.

In one embodiment, the host cell is a genetically-modified *Shigella, Yersinia, Salmonellia* and *Escherichia* sp. bacteria containing a mutation in at least one gene which inhibits the extracellular secretory pathway.

Various *E. coli* strains may be mutated to contain a mutation in one or more genes selected from ompR, envZ, nlpD, entC, entE, yebE, yihF, yebG, mzrA, ftsK, tnaA, ompC, and ompF. Wild-type *E. coli* strains may be any *E. coli* strains that are found in natural populations. Examples include the *E. coli* strain BW25113, HB101, HMS174, BLR, TOP10, W3110 (ATCC Accession No. 27325) and the MG1655 (ATCC Accession No. 47076), 294 (ATCC Accession No. 31,446), *E. coli* B (ATCC Accession No. 11303), X1776 (ATCC Accession No. 31,537), *E. coli* W (ATCC Accession No. 9637), DH1 (ATCC Accession No. 33,849) and KO11 (ATCC Accession No. 55,124).

The *E. coli* mutant strain can be obtained by any method. In one embodiment, a gene or DNA on the *E. coli* chromosomal DNA is deleted. For example, a gene can be deleted using homologous recombination in a strain expressing the lambda red recombinase system. In *E. coli*, homologous recombination usually requires a helper such as the lambda red system developed by Datsenko and Wanner. *Proc Natl Acad Sci USA*. 2000 Jun. 6; 97(12):6640-5. Homologous recombination involves the use of DNA fragments located at both outer sides of the gene that is intended to be deleted. An example of a DNA that can be used for homologous recombination include, but is not limited to, a linear DNA comprising, at both ends of a selectable marker gene, DNA that is homologous to chromosomal DNA into which the introduction of deletion, substitution or addition of nucleotide(s) is desired.

DNA that exists at both ends of the linear DNA is oriented on the linear DNA in the same direction as the chromosomal DNA. The length of the homologous region is suitably about 10 bp to 100 bp, about 20 bp to 50 bp, or about 30 bp to 40 bp. The homologous region will typically be 80% or more, suitably 95% or more, more suitably 100% homology. Homology of the nucleotide sequences can be determined using programs such as BLAST or FASTA. The DNA fragments can be prepared by PCR based upon the published sequences of the target gene(s), e.g., ompR, envZ, nlpD, entC, entE, yebE, yihF, yebG, mzrA, ftsK, tnaA, ompC, and ompF. Genomic DNA from the desired host strain can be used as a template for the PCR.

After the DNA for homologous recombination is introduced into a host cell by a conventional method, such as electroporation, transformants are selected using the selectable marker, e.g., antibiotic resistance, as an indicator. The transformants are cultured in a medium that does not contain the antibiotic for several hours to 1 day, and then the cultures are plated on a medium that contains the antibiotic. By determining the nucleotide sequence of a region of the chromosomal DNA in which the gene or DNA to be deleted was present, the deletion of the target gene or DNA on chromosomal DNA can be confirmed.

Any selectable marker gene can be used, provided that such genes impart resistance to an agent to which *E. coli* shows sensitivity. For example, kanamycin-resistant genes, chloramphenicol-resistant genes, gentamicin-resistant genes, spectinomycin-resistant genes, tetracycline-resistant genes, or ampicillin-resistant genes can be used as the selectable marker genes.

*E. coli* mutant strains can also be obtained using phage transduction of DNA from a donor strain to a recipient strain. In this case the donor strain mutation has typically been previously characterized and confers at least one selectable phenotype.

Expression Vectors for Secretion of Recombinant Proteins

The secreted recombinant proteins invention can be produced through the application of recombinant DNA technology. Recombinant constructs encoding a protein of interest typically include an expression control sequence operably-linked to the coding sequences of the protein of interest. A "recombinant protein of interest" refers to a protein, the production of which may be deemed desirable for any reason. Such proteins may include enzymes, antibodies, etc., or portions thereof. The protein may be of interest for commercial and/or therapeutic purposes. A nucleotide sequence "encodes" or "codes for" a protein if the nucleotide sequence can be translated to the amino acid sequence of the protein. The nucleotide sequence may or may not contain an actual translation start codon or termination codon.

For expression of the recombinant protein of interest, the nucleic acid containing all or a portion of the nucleotide sequence encoding the protein of interest is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Lerner et al., U.S. Pat. No. 6,291,160; 6,680,192. Vectors can also encode secretory protein or signal peptide, e.g., YebF, SEC, TAT, pectate lyase, etc., which are useful to direct the secretion of the peptide of interest to the periplasm or extracellular medium.

In general, expression vectors useful in recombinant DNA techniques are often in the form of plasmids. In the present specification, "plasmid" and "vector" can be used interchangeably as the plasmid is the most commonly used form of vector. However, the technology is intended to include such other forms of expression vectors that are not technically plasmids, which serve equivalent functions.

The recombinant expression vectors include a nucleic acid encoding a protein of interest in a form suitable for expression of the nucleic acid in a host cell, which means that the recombinant expression vectors include one or more regulatory sequences, selected on the basis of the host cells to be used for expression that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence. The term "regulatory sequence" is intended to include promoters, enhancers and other expression control elements. Such regulatory sequences are described, e.g., in Goeddel, Gene Expression Technology Methods in Enzymology 185, Academic Press, San Diego, Calif. (1990). Regulatory sequences include those that direct constitutive expression of a nucleotide sequence in many types of host cell and those that direct expression of the nucleotide sequence only under certain conditions, i.e. inducible promoters. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides, encoded by nucleic acids as described herein. One such example is the expression of heterologous proteins through chromosomal insertion.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors serve four purposes: (i) to direct secretion of the polypeptide from the cell; (ii) to increase expression of recombinant polypeptide; (iii) to increase the solubility of the recombinant polypeptide; and (iv) to aid in the purification of the recombinant polypeptide by acting as a ligand in affinity purification. In some embodiments, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

In some embodiments, the expression vectors can encode a secretory sequence or signal peptide, e.g., YebF, SEC, TAT, etc. as described above, which are useful to direct the secretion of the peptide of interest. In one embodiment, the secretory sequence is YebF. For example, the recombinant protein of interest may be constructed as a C-terminal fusion to YebF. In one embodiment, YebF has the sequence according to SEQ ID NO: 1 below:

```
                                   (SEQ ID NO: 1)
MKKRGAFLGLLLVSACASVFAANNETSKSVTFPKCEGLDAAGIAAS

VKRDYQQNRVARWADDQKIVGQADPVAWVSLQDIQGKDDKWSVPLT

VRGKSADIHYQVSVDCKAGMAEYQRR
```

In one embodiment, YebF is encoded by the sequence according to SEQ ID NO: 2 below:

```
                                   (SEQ ID NO: 2)
ATGAAAAAAAGAGGGGCGTTTTTAGGGCTGTTGTTGGTTTCTGCCT

GCGCATCAGTTTTCGCTGCCAATAATGAAACCAGCAAGTCGGTCAC

TTTCCCAAAGTGTGAAGATCTGGATGCTGCCGGAATTGCCGCGAGC

GTAAAACGTGATTATCAACAAAATCGCGTGGCGCGTTGGGCAGATG

ATCAAAAAATTGTCGGTCAGGCCGATCCCGTGGCTTGGGTCAGTTT

GCAGGACATTCAGGGTAAAGATGATAAATGGTCAGTACCGCTAACC

GTGCGTGGTAAAAGTGCCGATATTCATTACCAGGTCAGCGTGGACT

GCAAAGCGGGAATGGCGGAATATCAGCGGCGTTAA
```

In some embodiments, signal peptides may be used to export proteins to the periplasm between the inner and outer membranes. By placing a signal sequence in front of the coding sequence of the desired protein, the expressed protein can be directed to a particular export pathway (U.S. Pat. Nos. 5,047,334, 4,963,495.). Known export pathways in *E. coli* include the SecB-dependent (SEC), the twin-arginine translocation (TAT), and the signal recognition particle (SRP) pathway. Translocation in the SEC or TAT pathway is via a post-translational mechanism, whereas the SRP pathway translocation is co-translational. Proteins translocated by the SEC pathway are unfolded prior to export and then refolded in the periplasm. In the TAT pathway, the proteins are translocated in a folded state.

Examples of other signal sequences that could be used to secrete proteins in *E. coli* include, but are not limited to, Pectate lyase B (PelB) from *Erwinia carotovora*; Outer-membrane protein A (OmpA); Heat-stable enterotoxin 2 (StII); Endoxylanase (Endo) from *Bacillus* sp.; Alkaline phosphatase (PhoA); Outer-membrane pore protein F (OmpF); Outer-membrane pore protein E (PhoE); Maltose-binding protein (MalE); Outer-membrane protein C (OmpC); Murein lipoprotein (Lpp); Lamba receptor protein (LamB); Protease VII (OmpT); and Heat-labile enterotoxin subunit B (LTB).

One strategy to maximize recombinant polypeptide expression in *E. coli* is to express the polypeptide in host bacteria with an impaired capacity to proteolytically cleave the recombinant polypeptide. See, e.g., Gottesman, Gene Expression Technology: Methods in Enzymology 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (see, e.g., Wada, et al., 1992. *Nucl. Acids Res.* 20: 2111-2118). Such alteration of nucleic acid sequences of the invention can be carried out by standard DNA synthesis techniques.

Expression and Secretion of Recombinant Proteins

In one aspect, the disclosure pertains to mutant host cells into which a recombinant expression vector has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation, biolistics or viral-based transfection can be used for other cellular hosts. Other methods used to transform mammalian cells include the use of polybrene, protoplast fusion, liposomes, electroporation, and microinjection (see generally, Sambrook et al., *Molecular Cloning.*, 2nd ed., Cold Spring Harbor Laboratory, Cold Spring Harbor Laboratory Press, Cold Spring Harbor, N.Y., 1989). Suitable methods for transforming or transfecting host cells can be found in Sambrook, et al., and other laboratory manuals. Host cells carrying the expression vector are identified through the use of the selectable marker, and the presence of the gene of interest is confirmed by hybridization, PCR, antibodies, or other techniques.

A mutant host cell that includes an expression vector, such as a prokaryotic host cell in culture, can be used to produce (i.e., express) the recombinant protein of interest. In one embodiment, the method comprises culturing the mutant host cell of invention (into which a recombinant expression vector encoding the protein of interest has been introduced) in a suitable medium such that the protein of interest is produced. In another embodiment, the method further comprises the step of isolating the protein of interest from the medium or the host cell. Once expressed, collections of the protein of interest are purified from culture media and host cells. The protein of interest can be purified according to standard procedures of the art, including HPLC purification, column chromatography, gel electrophoresis and the like. Usually, the protein of interest is expressed with signal sequences and are thus released to the culture media.

The host cells are grown in growth medium until such time as is desired to harvest the secreted protein. The time required depends upon a number of factors relating to the bacterial expression system being used and to the protein produced. The rate of growth of a particular bacterial strain or species; the rate at which the secreted target protein accumulates in the periplasm or extracellular medium; the stability of the secreted protein; and the time at which bacterial lysis begins to occur (which will contaminate the medium) are examples of the types of considerations that will affect when the secreted protein is harvested from the periplasm or extracellular medium.

In the case of intracellular production, the cells are harvested and the protein, polypeptide or peptide is released from the periplasm into the extracellular medium by inducing outer membrane leakage or rupturing the cells using mechanical forces, ultrasound, enzymes, chemicals and/or high pressure. Following secretion into the medium (for example, via YebF), the protein, polypeptide or peptide may be extracted from the medium. Depending upon the level of purity required, which will again depend upon the application for which the secreted recombinant protein, polypeptide or peptide will be used, the secreted protein may be further purified, for example by chromatography (e.g., affinity chromatography), precipitation, ultrafiltration, electrophoresis, or other suitable techniques.

Purification of recombinant polypeptides is well known in the art and include ammonium sulfate precipitation, affinity chromatography purification technique, column chromatography, ion exchange purification technique, gel electrophoresis and the like (see generally Scopes, Protein Purification (Springer-Verlag, N.Y., 1982).

Uses

In one aspect, the bacteria described herein may be useful for manufacturing a variety proteins. In some embodiments, the bacteria are engineered to produce proteins needed for bioenergy production, therapeutic biologics, and research tools. The present technology provides significant advantages over current techniques. Because the proteins are exported, there is a significantly lower level of contamination, endotoxin, host cell proteins and nucleic acids, making purification easier and thus lowering production cost and durations. Importantly, the invention enables the production of proteins which might otherwise not be expressed due to toxicity and folding errors. The technology may be used for rapid production of proteins at a commercial scale, adapted to high throughput protein production, or readily employed in automated systems.

In one embodiment, the mutant host strains and expression systems are used in the manufacture of cellulosic biofuels. Cellulosic biofuels are produced using secreted enzyme complexes including cellulases and xylanases. The cellulosic substrates cannot be imported into the cell. Therefore, the enzyme must be secreted. Providing a microorganism that could supply secreted enzyme complexes would greatly enhance biofuel production.

EXAMPLES

The present invention is further illustrated by the following examples, which should not be construed as limiting in any way.

Example 1

Identification of Mutants Affecting YebF-Mediating Secretion

We identified six *E. coli* genes whereby the deletion of each gene results in improved YebF-mediated secretion: ompR; envZ; nlpD; entC; yebE; and yihF. Mutants in each of these genes were identified and tested as described in this Example.

Strains. *E. coli* K-12 BW25113 is the parental strain in the Keio collection of knockouts from which all strain construction was performed. The initial host strain is the Keio dsbA knockout with the kanamycin resistance cassette removed. All subsequent deletions (i.e. entC, envZ, nlpD, ompR, yebE, and yihF) and deletion combinations were transduced into this strain. Removal of the kanamycin resistance cassette was performed between each transduction utilizing the FLP recombinase described by Datsenko and Wanner (Proc Natl Acad Sci USA. 2000 Jun. 6; 97(12):6640-5). In addition, each of these knockout strains was picked from the Keio collection to create the phage lysate for transduction.

Plasmids. Three plasmids were used in these Examples and are all contained in the pTRC99a vector backbone. The YebF sequence was modified to include a 6×His tag (SEQ ID NO: 6) and a FlAsH tag (-CCPGCC-(SEQ ID NO: 7)) on the protein carboxy terminus. All plasmid maps are shown in the attached sequence listing.

A brief summary of the workflow for the experiment was as follows.

(1) Generated lysate of knockout deletion;

(2) Transduced deletion into recipient strain;

(3) Removed antibiotic resistance marker;

(4) Transformed strain with expression construct (e.g. pTRC99a-YebF-FlAsH-His, pTRC99a-(Cm)-YebF-FlAsH-His; or pTRC99a-YebF-Cel5B);

(5) Induced expression with 0.1 mM IPTG;

(6) Assayed protein secretion by FlAsH fluorescence or western blot of His tag. The FlAsH tag reacts with the FlAsH-EDT reagent (Invitrogen) to produce a fluorescent product. The actual fluorescence assay generated during the screen solicited the use of a construct using an ampicillin drug marker and the subsequent verification of the single and multiple deletion containing strains utilized a chloramphenicol resistance marker. The western blot utilized a separate plasmid containing the YebF fused with a cellulase gene (i.e. Cel5B).

Table 1 and FIG. 1 shows the result of FlAsH fluorescence for each deletion on YebF-mediated secretion. The strains identified show consistently higher secretion of both tagged YebF as well as YebF-cellulase fusions.

TABLE 1

| 1° Screening Score | 2° Screening | Locus | Description |
|---|---|---|---|
| 9.4 | +++ | envZ/ompR | 2-component osmolarity regulator |
| 12.2 | ++ | nlpD | Novel lipoprotein, function unknown |
| 8.9 | + | mzrA | Modulator of EnvZ/OmpR operon |
| 10.8 | ++ | ftsK | DNA translocase at septal ring sorting daughter chromsome |
| 6.2 | + | tnaA | Tryptophanase |
| 27.6 | + | entC/E | Isochorismate synth I & comp of enterobactin synth cmplx |
| 6.6 | 0 | yihF | Conserved protein, DUF945 family |
| N/A | N/A | yebE | Inner membrane protein |

Example 2

Figure 2:
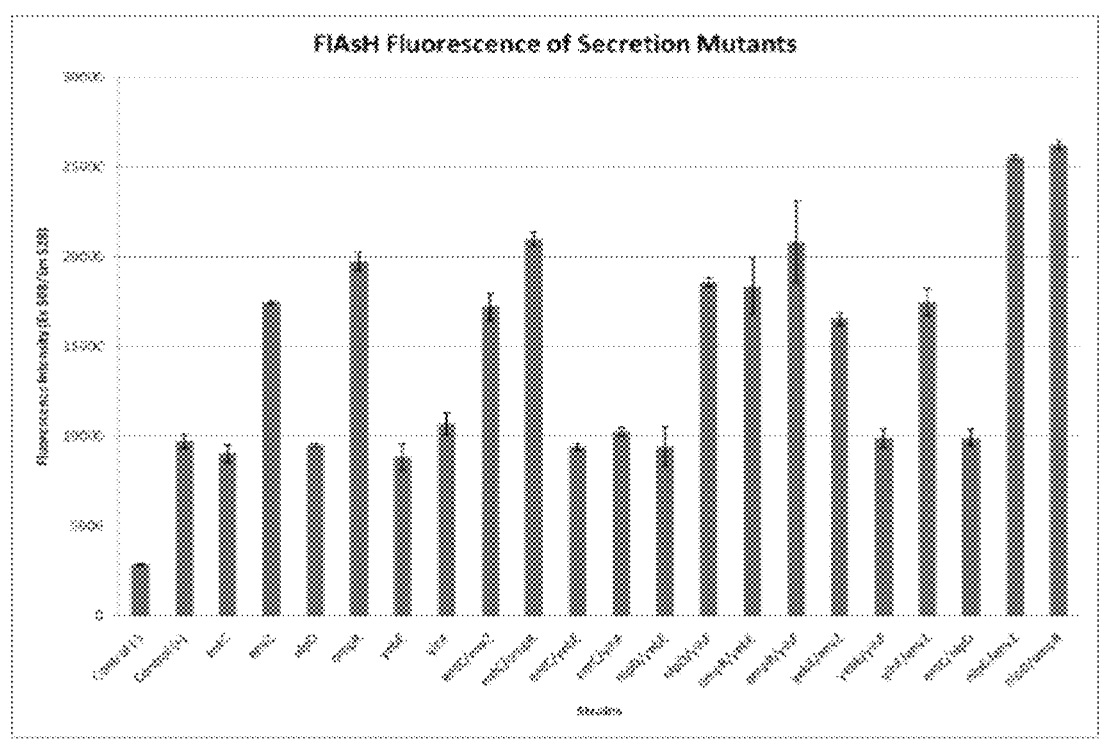
FIG. 2 is a graph showing the relative fluorescence from FlAsH-tagged YebF in *E. coli* having single- and double-mutations in YebF-related genes.
Figure 3:
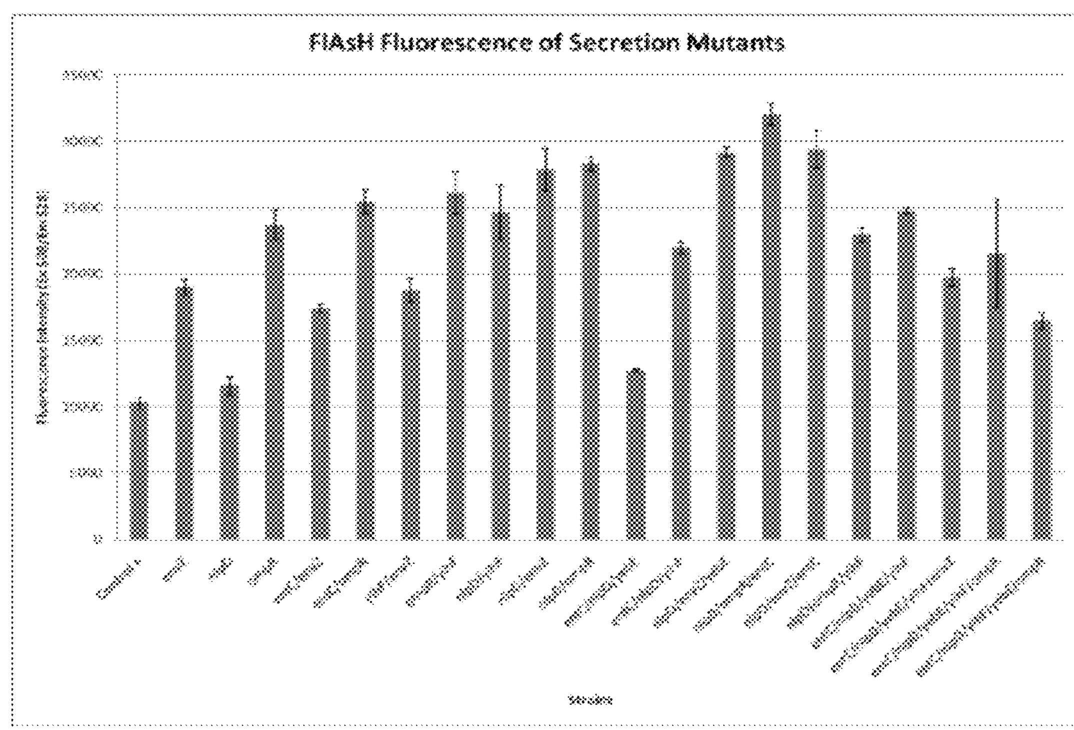
FIG. 3 is a graph showing the relative fluorescence from FlAsH-tagged YebF in *E. coli* having single- and multiple-mutations in YebF-related genes.

Comparison of Secretion in Single- and Multiple-Mutant *E. coli* Strains 96 deep-well plates were inoculated with all transformed secretion strains. A single colony from transformed plate was picked into 1.5 ml LB/Cm35. Plates were incubated at 30° C. while shaking in humidified shaker for 18-24 hours. The overnight cultures were subcultured at a 1:40 ratio into 1.5 mL media [LB/Cm35 (negative control) or LB/Cm35+0.1 mM IPTG]. Plated incubated overnight at 30° C. while shaking in humidified shaker for ~17-20 hrs. 200 μL of induced culture was assayed for secreted YebF protein by the addition of 10 μL of FlAsH/DTT/BAL cocktail (21 μM FlAsH-EDT, 21 mM DTT, and 5.25 mM 2,3-dimercaptopropanol) for a final concentration of 1 μM FlAsH-EDT, 1 mM DTT, and 250 μM 2,3-dimercaptopropanol. Plate incubated in a spectrophotometer for 20 minutes while measuring the optical density at 600 nm and fluorescence (Ex 508 nm/Em 528 nm) every minute. The data shown in FIG. 2 and FIG. 3 represent the fluorescence measurements after 20 minutes.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A recombinant bacterium transformed with a recombinant vector comprising a first DNA sequence encoding a YebF linked to a second DNA sequence encoding a heterologous protein, wherein the mutant bacterium comprises mutations so that at least the NlpD gene product and at least one of the EnvZ, OmpR and YihF gene products are not expressed or are rendered non-functional.

2. The recombinant bacterium of claim 1 wherein the bacterium is a gram negative bacterium.

3. The recombinant bacterium of claim 2, wherein the bacterium is selected from the group consisting of *Escherichia, Salmonella, Yersinia*, and *Shigella.*

4. The recombinant bacterium of claim 1, wherein both the NlpD and EnvZ gene products are not expressed or are rendered non-functional.

5. The recombinant bacterium of claim 1, wherein both the NlpD and OmpR gene products are not expressed or are rendered non-functional.

6. The recombinant bacterium of claim 1, wherein the NlpD and YihF gene products are not expressed or are rendered non-functional.

7. An expression system for secreting a recombinant protein into a culture medium, the system comprising: (a) a mutant *E. coli* bacterium, wherein the NlpD gene product and at least one of the EnvZ, OmpR and YihF gene products are not expressed or are rendered non-functional; and (b) a recombinant vector comprising a first DNA sequence encoding YebF linked to a second DNA sequence encoding a heterologous protein.

8. The system of claim 7, wherein both the NlpD and EnvZ gene products are not expressed or are rendered non-functional.

9. The system of claim 7, wherein both the NlpD and OmpR gene products are not expressed or are rendered non-functional.

10. The system of claim 7, wherein the NlpD and YihF gene products are not expressed or are rendered non-functional.

11. The system of claim 7, wherein the at least one gene product is not expressed or is rendered non-functional by deleting all or part of the gene encoding the gene product.

12. The system of claim 7, wherein the at least one gene product is not expressed or is rendered non-functional by way of alteration of a promoter control sequence.

13. The system of claim 7, wherein said recombinant vector further comprises an inducible promoter sequence element.

14. The system of claim 7, wherein said recombinant vector further comprises a repressor element.

15. The system of claim 7, wherein the heterologous protein that is secreted is biologically active.

16. The system of claim 7, wherein the heterologous protein is selected from the group consisting of: a cellulase, a protease, a lipase, a cutinase, an amylase, a galactosidase, a pullulanase, a glucose isomerase, a protein disuphide isomerase, a cyclodextrin gluconotransferase, a phytase, a glucose oxidase, a glucosyl transferase, laccase, bilirubin oxidase, a xylanase, an antigenic microbial or protozoan protein, a bacterial protein toxin, a viral protein, and a pharmaceutical.

17. The system of claim 7, wherein the heterologous protein is selected from the group consisting of an immunoglobulin light chain, an immunoglobulin heavy chain, an immunoglobulin light chain fragment or an immunoglobulin heavy chain fragment.

18. The system of claim 7, wherein the expression of both DNA sequences is under the control of an inducible promoter.

19. The system of claim 18, wherein the inducible promoter is a lac promoter.

* * * * *